(12) United States Patent
Kawamata et al.

(10) Patent No.: US 7,453,568 B2
(45) Date of Patent: *Nov. 18, 2008

(54) FLUORESCENCE OBSERVATION EQUIPMENT

(75) Inventors: Ken Kawamata, Hachioji (JP); Nobuyoshi Toyohara, Sagamihara (JP)

(73) Assignee: Olympus Corporation, Tokyo (JP)

( * ) Notice: Subject to any disclaimer, the term of this patent is extended or adjusted under 35 U.S.C. 154(b) by 303 days.

This patent is subject to a terminal disclaimer.

(21) Appl. No.: 10/533,687

(22) PCT Filed: May 19, 2004

(86) PCT No.: PCT/JP2004/006733

§ 371 (c)(1),
(2), (4) Date: May 2, 2005

(87) PCT Pub. No.: WO2005/001450

PCT Pub. Date: Jan. 6, 2005

(65) Prior Publication Data

US 2006/0017913 A1 Jan. 26, 2006

(30) Foreign Application Priority Data

Jun. 25, 2003 (JP) ............................. 2003-181614
Sep. 9, 2003 (JP) ............................. 2003-316995
Apr. 1, 2004 (JP) ............................. 2004-109327

(51) Int. Cl.
*G01J 3/30* (2006.01)
*F21V 9/16* (2006.01)

(52) U.S. Cl. ..................... 356/317; 356/300; 250/458.1

(58) Field of Classification Search ........................ None
See application file for complete search history.

(56) References Cited

U.S. PATENT DOCUMENTS

| | | | |
|---|---|---|---|
| 4,612,938 A | 9/1986 | Dietrich et al. | |
| 6,184,535 B1 | 2/2001 | Kashima et al. | |
| 6,603,140 B2 * | 8/2003 | Kobori et al. | 257/40 |
| 6,667,830 B1 * | 12/2003 | Iketaki et al. | 359/368 |
| 6,809,859 B2 * | 10/2004 | Erdogan et al. | 359/359 |
| 7,050,224 B2 * | 5/2006 | Kawamata et al. | 359/359 |
| 2003/0096322 A1 | 5/2003 | Guliano et al. | |

FOREIGN PATENT DOCUMENTS

| | | |
|---|---|---|
| JP | 07-134101 | 5/1995 |
| JP | 10-239517 | 9/1998 |
| JP | 2002-194529 | 7/2002 |
| JP | 2002-321939 | 11/2002 |
| JP | 2002-350347 | 12/2002 |
| JP | 2003-207451 | 7/2003 |

\* cited by examiner

*Primary Examiner*—Tarifur R Chowdhury
*Assistant Examiner*—Tara S Pajoohi
(74) *Attorney, Agent, or Firm*—Kenyon & Kenyon LLP

(57) ABSTRACT

An apparatus for fluorescence observation includes an excitation filter which transmits only exciting light of an specific wavelength among illumination light, and an absorption filter which blocks the exciting light and transmits only fluorescence generated from a specimen when the exciting light is irradiated to the specimen. Here, an interval of a half-value wavelength at a long-wavelength side of the excitation filter and a half-value wavelength at a short-wavelength side of the absorption filter is in a width between 1 nm to 6 nm, and change of the half-value wavelength of the excitation filter and the absorption filter when humidity changes from 10% to 95%, is 0.5 nm or less.

4 Claims, 11 Drawing Sheets

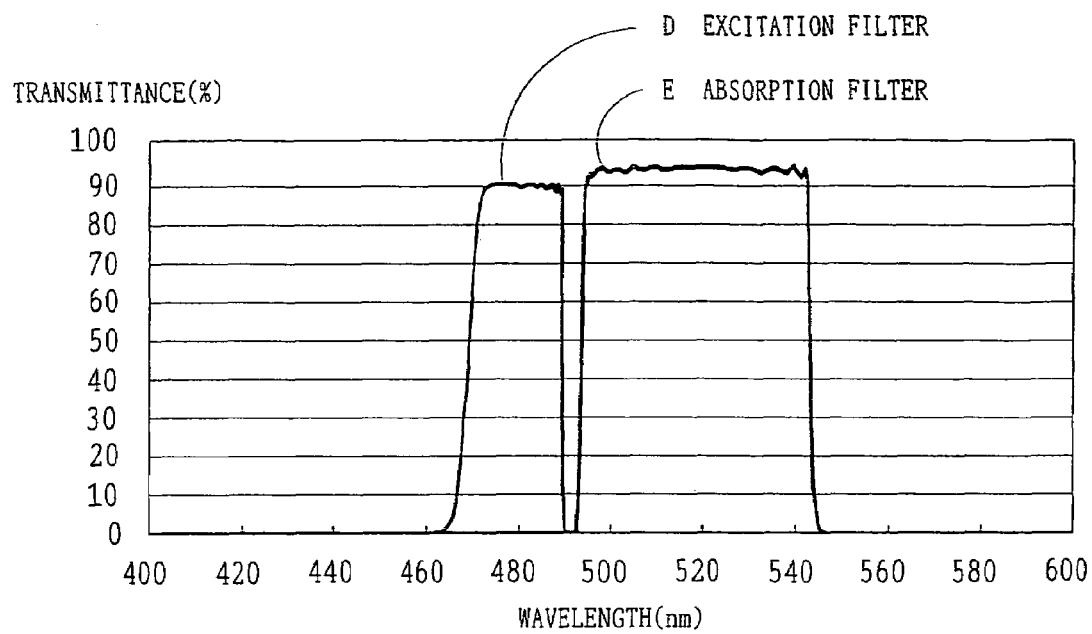
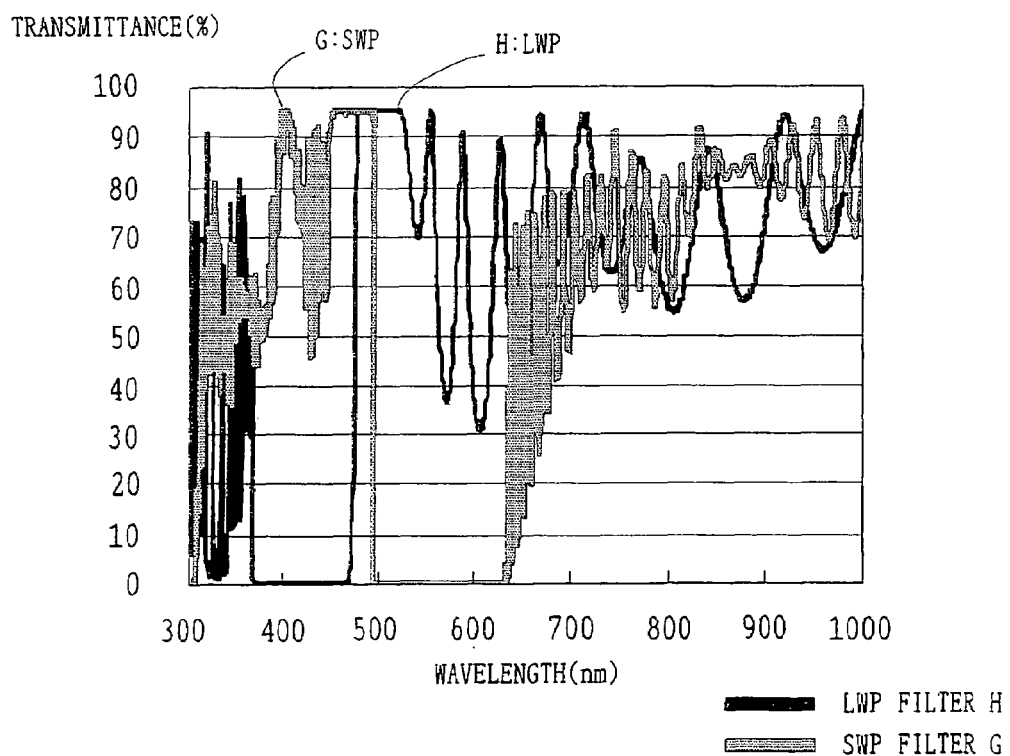

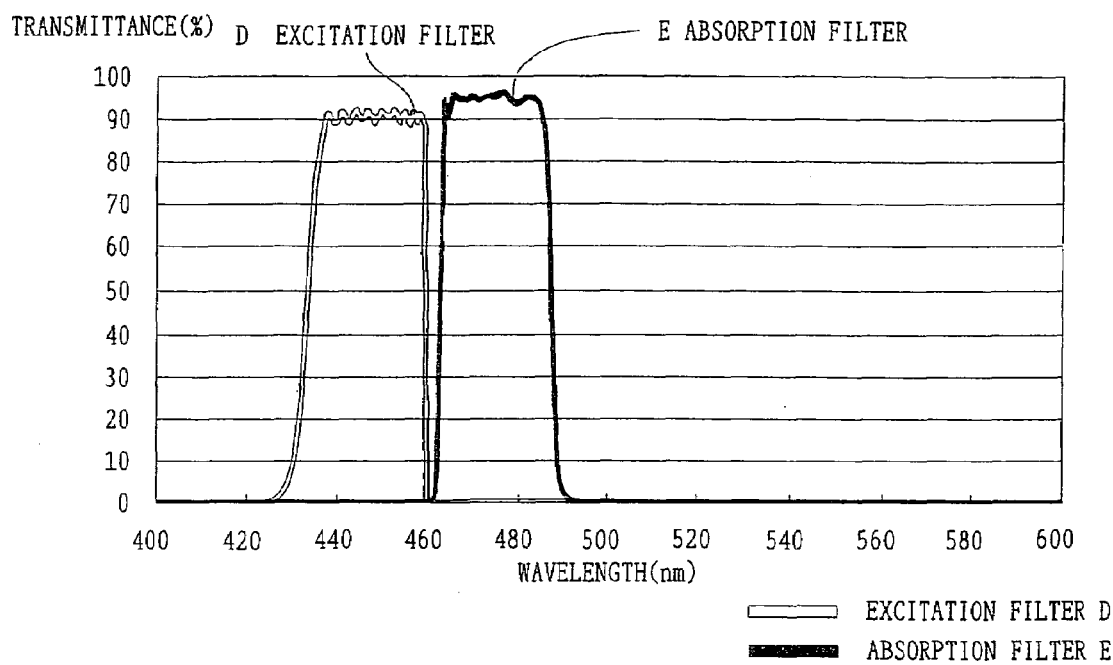
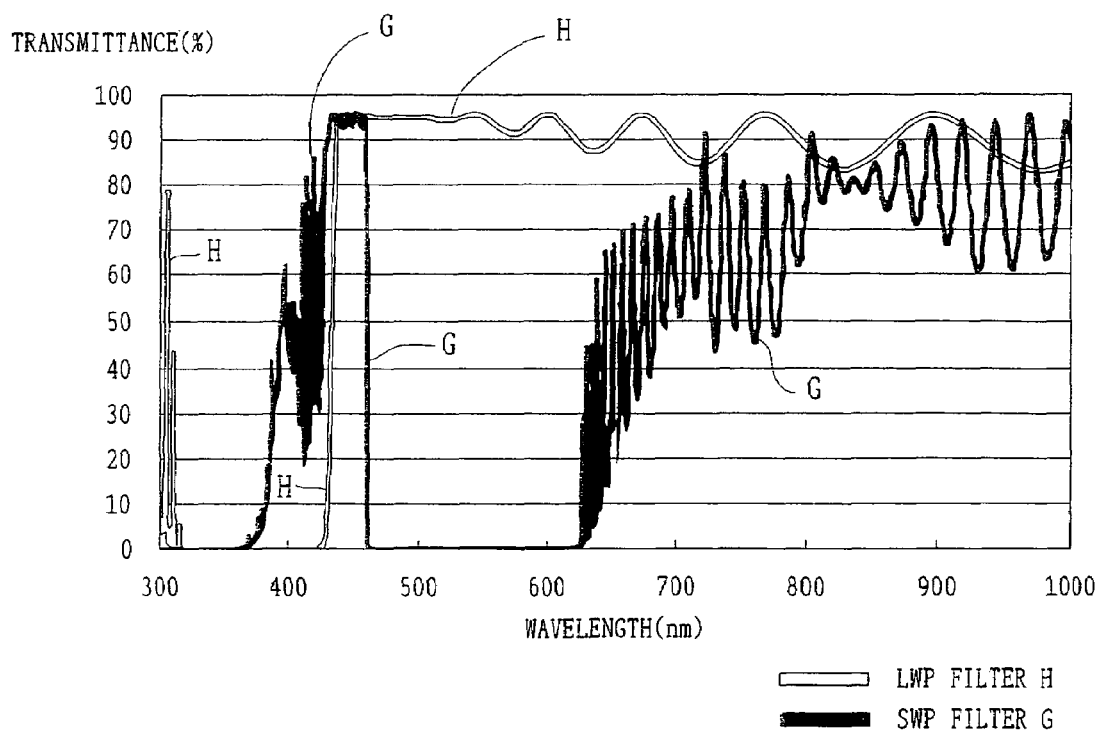

FLUORESCENCE OBSERVATION EQUIPMENT

This is a 371 national phase application of PCT/JP2004/006733 filed 19 May 2004, claiming priority to Japanese Patent Applications No. 2003-181614 filed 25 Jun. 2003, No. 2003-316995 filed 9 Sep. 2003, and No. 2004-109327 filed 1 Apr. 2004, the contents of which are incorporated herein by reference.

TECHNICAL FIELD

The present invention relates to an apparatus for fluorescence observation, such as a microscope and an endoscope which are used for fluorescence observation, and a measuring instrument for measuring an intensity of fluorescence.

BACKGROUND ART

So far, fluorescence observation using a microscope, an endoscope, etc. as an apparatus for the fluorescence observation, wherein exciting light is illuminated to a specimen of a living tissue etc., and only the fluorescence generated from the specimen is used, has been carried out.

In order to carry out this fluorescence observation, as for an apparatus for the fluorescence observation as a mechanism for fluorescence observation, an excitation filter which transmits only exciting light of a specific wavelength of illumination light, and an absorption filter which blocks the exciting light and transmits only the fluorescence generated from the specimen when the exciting light is illuminated to the specimen have been used. As another composition for carrying out the fluorescence observation, an absorption filter which blocks exciting light transmits and only the fluorescence generated from a specimen when laser light as exciting light is illuminated to the specimen has been used, wherein the laser light of a specific wavelength obtained from a laser source in which a wavelength selection element, such as etalon and the like, is combined with a dye laser, as illumination light is used.

Conventionally, an endoscope which is used for the fluorescence observation, has been disclosed in Japanese Unexamined Patent Application Toku Kai Hei No. 10-239517, for example. In the endoscope disclosed here, fluorescence observation is carried out by such a way that light having wavelength of 460 nm or less, as exciting light, transmits an excitation filter, and it is irradiated to a living tissue, and the exciting light reflected from the living tissue is cut off by the absorption filter, which transmits the fluorescence having wavelength from about 480 nm to 585 nm generated from the living tissue excited by the exciting light, and an image of this fluorescence is formed on a CCD camera through an image forming optical system.

Generally, the fluorescence generated from a specimen is weak. For this reason, in the fluorescence observation, it becomes important to pick up only the fluorescence efficiently. It is determined by the performance of an excitation filter, an absorption filter, etc. whether only the fluorescence can be picked up efficiently or not.

FIG. 18 is a spectrum characteristic graph showing exemplarily a relation that fluorescence 62 having a longer wavelength range than the wavelength range of exciting light 61 is generated by radiating exciting light 61 to a specimen when the fluorescence observation is carried out by radiating the exciting light 61 having a predetermined spectrum characteristic. The intensity of light of the fluorescence 62 is very weak compared with the intensity of the exciting light 61. As shown in FIG. 18, the wavelength range of the exciting light 61 and the wavelength range of the fluorescence 62 overlap partially. Then, in order to keep the exciting light 61 from overlapping in a wavelength range of peak 62a of the fluorescence 62, it is made to transmit an excitation filter 63, and the light in a wavelength range which does not overlap with the peak 62a of the fluorescence 62 is set as exciting light which is irradiated to the specimen.

The fluorescence 62 is generated by radiating this exciting light 61 to the specimen. In order to pick up and observe the fluorescence only as much as possible, it is desirable that an absorption filter 64 has a portion in which the fluorescence intensity is much at the right and the left sides of the peak 62a of the fluorescence 62 out of generated fluorescence, that is, a spectrum characteristic which transmits light in a wavelength range of the high transmission ratio efficiently. However, since it is desired to avoid that the exciting light irradiated to the specimen enters into the observation side, it is necessary to cut off completely the exciting light by the absorption filter 64. On the other hand, for generating much the fluorescence 62, it is desirable that the excitation filter 63 for determining a wavelength range of the exciting light which is irradiated to the specimen has such spectrum characteristic that the light in a wavelength range (wavelength band) at both sides of the peak 61a of the exciting light 61 is broad as much as possible so as to transmit the exciting light 61 within the wavelength range.

For this, it is desirable that an interval C (wavelength width) is narrow as much as possible and there is no overlapped portion, where the interval C represents an interval between a half-value wavelength A at the long-wavelength side within a wavelength range of the exciting light 61 penetrating the excitation filter 63 (the half-value wavelength A represents a wavelength at the long-wavelength side, wherein a transmittance of the excitation filter 63 becomes a half of the maximum value in the spectrum characteristic graph of FIG. 18. Hereafter, the half-value wavelength A is defined as "a half-value wavelength at the long-wavelength side of an excitation filter"), and a half-value wavelength B at the short-wavelength side in the wavelength range of the fluorescence 62 which transmits the absorption filter 64 (the half-value wavelength B represents a wavelength at the short-wavelength side, wherein transmittance of the absorption filter 64 becomes a half of the maximum value in the spectrum characteristic graph of FIG. 18. Hereafter, a half-value wavelength B is defined as "a half-value wavelength at the short-wavelength side of an absorption filter"). (here, a half-value wavelength means a wavelength when transmittance becomes a half of the maximum transmittance in a spectrum characteristic graph showing a transmittance to each wavelength, that is, it is a wavelength when the transmittance becomes a half)

However, so far, because the performance of the excitation filter and the absorption filter are bad, fluorescence has not been picked up efficiently. For this reason, in order to keep the exciting light from being mixed in the fluorescence, the interval C between the half-value wavelength A at the long-wavelength side of the excitation filter 63 and the half-value wavelength B at the short-wavelength side of the absorption filter 64 is set about 20 nm which is about the wavelength width. Since such light in this wavelength range of about 20 nm has not been used as fluorescence or as exciting light, there is a problem that it has been of no use. This problem is also the same when using laser light as illumination light. That is, since light within a wavelength width between "a wavelength of laser light" and "a half-value wavelength at the short-wavelength side of the absorption filter" has not been used as fluorescence or as exciting light, there was a problem that it has been of no use.

The present invention has been made in consideration of the above-mentioned problem, and it aims at offering an observation apparatus for fluorescence which can pick up weak fluorescence efficiently in the fluorescence observation using an excitation filter and an absorption filter, or in the fluorescence observation using a laser and an absorption filter.

DISCLOSURE OF THE INVENTION

In order to attain the purposes mentioned above, the apparatus for fluorescence observation according to the present invention comprises an excitation filter which transmits only exciting light of an specific wavelength in illumination light, and an absorption filter which blocks the exciting light and transmits only fluorescence generated from a specimen when the exciting light is irradiated to the specimen, wherein an interval between "a half-value wavelength at the long-wavelength side of the excitation filter" and "a half-value wavelength at the short-wavelength side of the absorption filter" is within a width between 1 nm to 6 nm.

The apparatus for fluorescence observation according to the present invention is constructed such that change of a half-value wavelength of the excitation filter and the absorption filter when humidity changes from 10% to 95%, is 0.5 nm or less.

The apparatus for fluorescence observation according to the present invention, the excitation filter and/or the absorption filter contain multilayer film having 90 or more layers.

The apparatus for fluorescence observation according to the present invention, the excitation filter and the absorption filter contain a multilayer film consisting of $SiO_2$ which is a low refractive index film, and $Ta_2O_5$, $Nb_2O_5$ or $TiO_2$, or a mixed film composed of mixture of any of these, each of which is a high refractive index film.

The apparatus for fluorescence observation according to the present invention is incorporated in an optical system of a microscope or an endoscope. In the apparatus for fluorescence observation according to the present invention, an excitation filter has, at least, a long wave pass (LWP) filter and a short wave pass (SWP) filter, wherein the long wave pass filter and the short wave pass filter are formed as a film on different substrates and assembled.

The apparatus for fluorescence observation according to the present invention comprises laser light used as exciting light and an absorption filter which blocks the exciting light, and transmits only the fluorescence generated from a specimen when the exciting light is irradiated to the specimen, wherein an interval between "a wavelength of the laser light" and "a half-value wavelength at the short-wavelength side of the absorption filter" is within the width between 1 nm to 12 nm.

The apparatus for fluorescence observation according to the present invention, it is composed that an interval between "a wavelength of the laser light" and "a half-value wavelength at the short-wavelength side of the absorption filter" is set within the width between 6 nm to 12 nm.

In the apparatus for fluorescence observation according to the present invention, it is constructed such that change of the half-value wavelength of the absorption filter when humidity changes from 10% to 95% is 0.5 nm or less.

In the apparatus for fluorescence observation according to the present invention, the absorption filter contains a multilayer film having 90 or more layers.

In the apparatus for fluorescence observation according to the present invention, a laminated portion composing the absorption filter consists of a multilayer in which films are alternately laminated, wherein a low refractive index film which is $SiO_2$, and a high refractive index film which is $Ta_2O_5$, $Nb_2O_5$, $TiO_2$, or a film composed of mixture of any of these, and the absorption filter comprises the multilayer in which films are alternately laminated, at least in one component of surfaces.

The apparatus for fluorescence observation comprises an excitation filter which transmits only exciting light having a specific wavelength out of illumination light, and an absorption filter which blocks the exciting light and transmits only fluorescence generated from the specimen irradiated with the exciting light, wherein the excitation filter and the absorption filter are composed so as to have such characteristics that an interval between a wavelength for which the excitation filter has transmittance of 0.1% on the long-wavelength side and a half-value wavelength of the excitation filter on the long-wavelength side is in a width between 0.1 to 5.9 nm, an interval between a wavelength for which the absorption filter has transmittance of 0.1% on the short-wavelength side and a half-value wavelength of the absorption filter on the short-wavelength side is in a width between 0.1 to 5.9 nm, an interval between the half-value wavelength of the excitation filter on the long-wavelength side and a wavelength for which the excitation filter has transmittance of 80% on the long-wavelength side is 5.9 nm or less, and an interval between the half-value wavelength of the absorption filter on the short-wavelength side and a wavelength for which the absorption filter has transmittance of 80% on the short-wavelength side is 5.9 nm or less.

In the apparatus for fluorescence observation according to the present invention, it is constructed such that change of the half-value wavelength of the excitation filter and the absorption filter when humidity changes from 10% to 95%, is 0.5 nm or less.

In the apparatus for fluorescence observation according to the present invention, the filter and/or the absorption filter contain a multilayer film having 90 or more layers.

In the apparatus for fluorescence observation according to the present invention, a laminated portion composing the excitation filter and the absorption filter consists of a multilayer in which films are alternately laminated, wherein a low refractive index film which is $SiO_2$, and a high refractive index film which is $Ta_2O_5$, $Nb_2O_5$, $TiO_2$, or a film composed of mixture of any of these, and, the excitation filter and the absorption filter comprise the multilayer in which films are alternately laminated, at least in one component of surfaces.

The apparatus for fluorescence observation according to the present invention can be incorporated in an optical system of a microscope.

Moreover, the apparatus for fluorescence observation according to the present invention can be incorporated in an optical system of an endoscope.

According to the present invention, in an apparatus for fluorescence observation using an excitation filter and an absorption filter, or using laser light and an absorption filter, an apparatus for fluorescence observation by which weak fluorescence can be picked up efficiently and a high sensitive fluorescence intensity measurement with bright image observation can be obtained.

Purposes, features, and advantages other than the above mentioned of the present invention will become clear by the following detailed description with reference to the accompanying drawings.

BRIEF EXPLANATION OF DRAWINGS

FIG. 2 is a graph showing transmittance characteristics of an excitation filter and an absorption filter used for the first embodiment.

FIG. 3 is graph which shows optical characteristics of a long wave pass filter and a short wave pass filter which constitute the excitation filter shown in FIGS. 1 and 2.

FIG. 9 is a graph showing transmittance characteristics of an excitation filter and an absorption filter used for the third embodiment according to the present invention.

FIG. 10 is a graph showing optical characteristics of a long wave pass filter and a short wave pass filter which constitute the excitation filter shown in FIG. 9.

BEST MODE FOR CARRYING OUT THE INVENTION

Figure 1:
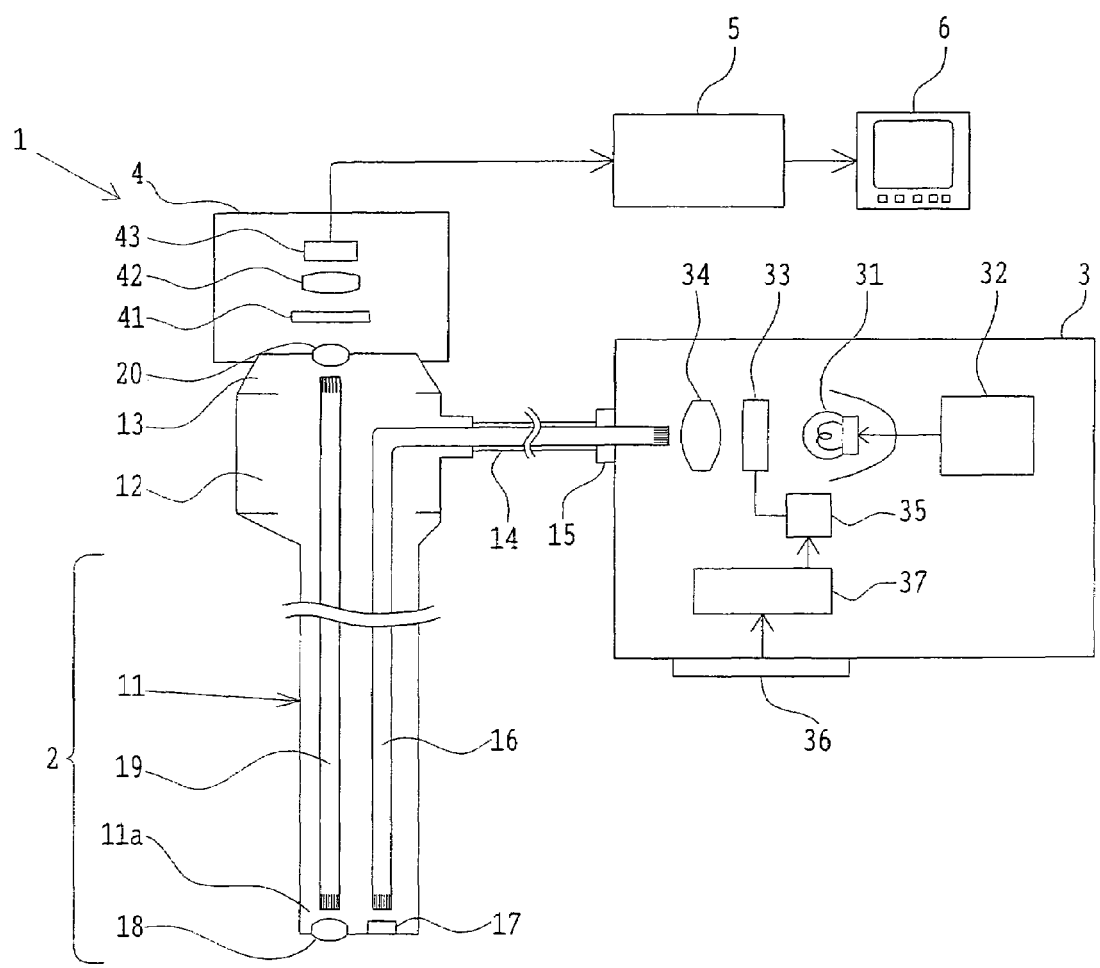
FIG. 1 is an outline composition diagram of the first embodiment of the apparatus for fluorescence observation according to the present invention.

Prior to explaining embodiments, function and advantages of the present invention will be explained.

Reasons why an interval of a half-value wavelength at a long wave side of an excitation filter and a half-value wavelength at a short-wavelength side of an absorption filter is separated are as follows. They are caused by (1) stability of spectrum characteristic of a filter is not enough, and (2) the number of layers of a filter film is made about 50 layers.

The reason (1), that is, "stability of spectrum characteristics of a filter is not enough" is due to the fact that since a conventional filter is formed by vacuum evaporation method and the density of each film is not enough, a spectrum characteristic of the filter is shifted to a short-wavelength side or a long-wavelength side rather than a designed wavelength, by absorbing or discharging moisture into multilayer film owing to ambient humidity where the filter is used. By this, it is possibly supposed that the shift of about ±5 nm arises. Even if there is such shift, since the half-value wavelength at a long wave side of an excitation filter and the half-value wavelength at a short-wavelength side of an absorption filter must not be overlapped when fluorescence is observed, it is necessary to keep a large interval (wavelength width) between the half-value wavelength at a long wave side of an excitation filter and the half-value wavelength at a short-wavelength side of an absorption filter when the apparatus is designed.

Here, "not be overlapped" is defined as follows. That is, it is defined as a characteristic wherein at the long-wavelength side of the excitation filter and the short-wavelength side of the absorption filter, transmittances of both sides are approaching to 0% infinitely, and it has such characteristic that a transmittance at the wavelength at which both intersect is 0.1% or less, or preferably 0.01% or less, or more preferably 0.001% or less.

Characteristic at the long-wavelength side of the absorption filter can be determined according to the fluorescence in fluorescence observation. A half-value width of the absorption filter having characteristic of a band pass filter (filter which transmits only a specific wavelength and cuts other wavelengths) is preferably 20 nm to 80 nm and more preferably 20 nm to 70 nm.

As for the half-value wavelength at the short-wavelength sides of the excitation filter, the more quantity of the exciting light can be irradiated to the specimen, as it is more departed from the half-value wavelength at the long wave side of the excitation filter. Since the exciting light becomes weak when a half-value width of the excitation filter is too short, the half value width of the excitation filter is preferably 15 nm to 70 nm and more preferably 15 nm to 60 nm.

The reason (2), that is, "the number of layers of filter is made about 50 layers" mentioned above aims at that a rising slope line of the spectrum transmittance characteristic of the half-value wavelength at the long wave side of the excitation filter or the half-value wavelength at the short-wavelength side of the absorption filter is made steep by increasing the number of layers of the film, and transmission areas of two filters are not overlapped. However, in a vacuum evaporation method used conventionally for formation of film, the number of layers of filter film is held down to about 50 layers, in fact, according to a problem of the manufacture error by the variation in film thickness, or a problem of adhesion between a substrate and a film, or between films each other, etc. However, like the present invention, if the interval of the half-value wavelength at the long wave side of the excitation filter and the half-value wavelength at the short-wavelength side of the absorption filter is made 1 nm to 6 nm smaller than those of the conventional one, weak fluorescence can be picked up efficiently and can be observed. In order to realize this, if a filter in which change of the half-value wavelength of the excitation filter and the absorption filter is 0.5 nm or less when humidity changes from 10% to 95%, is used, the reason (1) mentioned above can be removed. If the spectral characteristic of the filter does not almost shift, transmission areas of two filters are not overlapped by change of ambient humidity.

As a film forming method of the filter, it is desirable that the ion assist method, the ion plating method, the sputtering method, etc., are used, where a film density becomes higher than that in the conventional vacuum evaporation method. Contrary to the vacuum evaporation method where the a film formed tends to absorb water moisture as the film density is low density, in such film forming methods mentioned above, a hard film can be obtained without absorbing water, since the film density is high. Therefore, it has a feature that adhesion of the film is also improved. Therefore, even in a multilayer film having 50 layers and more, peeling or degradation of the film is few. If an excitation filter and/or an absorption filter is composed of a multilayer film having 90 or more layers in the present invention by utilizing these characteristics, the reason (2) mentioned above can be removed. Thereby, if a wavelength width between the half-value wavelength at the long wave side of the excitation filter and the half-value wavelength at the short-wavelength side of the absorption filter, which is determined by each spectrum characteristic or spectrum transmittance characteristic of the excitation filter and the absorption filter, that is, an interval between the half-value wavelength of two filters is narrowed, overlapping of transmission areas can be avoided. Such filter can be formed by a multilayer film which consists of, for example, mixture of $SiO_2$ and $Ta_2O_5$, or $SiO_2$ and $Nb_2O_5$, or $SiO_2$ and $TiO_2$, or mixture of either of $Ta_2O_5$, $Nb_2O_5$ or $TiO_2$, and $SiO_2$. Furthermore, the apparatus according to the present invention can be incorporated in an optical system of an endoscope or a microscope for fluorescence observation, or an optical system of an apparatus in which fluorescence intensity is measured and observed.

Moreover, like the present invention, if an interval of the half-value wavelength at the long wave side of the excitation filter and the half-value wavelength at the short-wavelength side of the absorption filter, that is, a wavelength width is made a width from 1 nm to 12 nm, which is narrower than 20 nm of the conventional one, a weak fluorescence can be efficiently observed. When fluorescence generated by laser light has a sufficient brightness, the laser light is kept from leaking to the observation side, by securing the interval of the wavelength of the laser light and the half-value wavelength at a short-wavelength side of an absorption filter. It is good that the width is made from 6 nm to 12 nm, taking into consideration of easy manufacture of the absorption filter.

In the present invention, also as mentioned above, in order to remove the reasons (1) and (2), the following measures can be taken such as measures using a filter in which change of the half-value wavelength of the excitation filter and the absorption filter is 0.5 nm or less when humidity changes from 10% to 95%, and measures for forming the absorption filter containing a multilayer film having 90 or more layers, for example, which is formed by a multilayer film consisting of, for example mixture of $SiO_2$ and $Ta_2O_5$, or $SiO_2$ and $Nb_2O_5$, or $SiO_2$ and $TiO_2$, or mixture of either of $Ta_2O_5$, $Nb_2O_5$ or $TiO_2$, and $SiO_2$, by using the ion assist method, the ion plating method, the sputtering method, etc.

Furthermore, the apparatus according to the present invention can be incorporated in an endoscope or a microscope for fluorescence observation, a measuring apparatus or the like in which fluorescence intensity is measured.

Next, embodiments of the present invention will be explained using drawings.

First Embodiment

FIG. 1 is an outline composition diagram of an endoscope for medical treatments for diagnosing existence of a disease of an organism etc, by carring out fluorescence observation and its optical system of the first embodiment of the apparatus for fluorescence observation according to the present invention.

This apparatus for fluorescence observation 1, comprises, as shown in FIG. 1, an endoscope 2 which is inserted into an abdominal cavity etc., and obtains an observation image of a tissue for observation, a light source 3 which supplies an illumination light to the endoscope 2, an image pick-up apparatus 4 which picks up the observation image obtained with the endoscope 2, and obtains an image pick-up signal, and a video processor 5 which changes the image pick-up signal acquired by the image pick-up apparatus 4 into the picture signal in which a monitor display is possible, and a monitor equipment 6 which shows the picture signal obtained by the video processor 5.

The endoscope 2 comprises a long and thin insertion portion 11 inserted into the abdominal cavity etc., and a control unit 12 which is arranged at an end portion side of the insertion portion 11, for gripping and operating the endoscope 2, an eyepiece portion 13 which is arranged at the end portion side of the control unit 12 and projects an observation image obtained with the endoscope 2, a light guide cable 14 extended from the side portion of the control unit 12 and receives supply of illumination light from the light source 3, a light guide connector 15 which is arranged at the end of the light guide cable 14, and connected with the light source 3, where attachment and detachment can be made freely, a light guide fiber 16 which guides the illumination light obtained from the light source 3 to an end portion 11a of the insertion portion 11 through the inside of the light guide cable 14, the control unit 12, and the insertion portion 11, and via the light guide connector 15, a light distribution optical system 17 which distributes the illumination light which is arranged at the end portion 11a, and is guided by the light guide fiber 16 to a portion for observation, an objective optical system 18 which is arranged at the end portion 11a and guides the optical image at the portion for observation into the endoscope 2, an image guide fiber 19 which guides the optical image which was guided by the objective optical system 18 to an eyepiece portion 13, through the inside of the insertion portion 11 and the control unit 12, and an eyepiece optical system 20 which ejects the optical image which is arranged at the eyepiece portion 13 and guided by the image guide fiber 19.

The light source apparatus 3 comprises an illuminant lamp 31 which emits an illumination light, and a power supply circuit 32 which supplies electric power to the illuminant lamp 31, an excitation filter 33 which is arranged in an illumination light path and transmits a wavelength which excites a portion for observation, a light condensing optical system 34 which condenses an illumination light to a light entrance surface end of the light guide fiber 16, a motor 35 made to insert and pull out the excitation filter 33 on the illumination light path, a console panel 36 for inputting an operation instruction to the light source 3, a controlling circuit 37 which controls and drives at least the motor 35 according to operation of a console panel 36.

The image pick-up apparatus 4 comprises an absorption filter 41 which transmits a wavelength composition of the fluorescence from a living tissue which is emanated from the eyepiece portion 13 of the endoscope 2 and used as an observation light, and blocks exciting light irradiated to the living tissue, an image forming optical system 42 which forms an image of the observation light, and CCD 43 as an image pick-up means which obtains an image pick-up signal by picking up an observation image formed by the image forming optical system 42.

In the endoscope for medical use, which is composed as mentioned above, an illumination optical system is formed by a light guide fiber 16 which leads the illumination light from a luminant lamp 31 to a living tissue and the luminant lamp 31, and the excitation filter 33 which transmits only the light having a specific wavelength as exciting light is inserted into the optical path of this illumination optical system. Meanwhile, an observation optical system is formed by the image guide fiber 19 in which the fluorescence generated from the living tissue enters, the eyepiece optical system 20 for observation and the imaging optical system 42, and the absorption filter 41 which transmits only the fluorescence used for observation is inserted in the optical path of this observation optical system. In this endoscope, by irradiating the exciting light which passes the excitation filter 33, fluorescence is generated from the living tissue and then the living tissue is observed on the basis of this fluorescence.

Here, the function of the endoscope for medical application of the first embodiment will be explained furthermore in detail. First, a tip end portion 11a is inserted in a position of the living tissue to which a fluorescence observation using an endoscope is carried out through the insertion portion 11. Then, the tip end portion 11a is mounted at the position in which the fluorescence observation can be carried out. Subsequently, the living tissue is put at a state in which fluorescence observation can be carried out.

Then, the motor 35 is operated by a console panel 36, and the excitation filter 33 is inserted in an illumination light path. Then, the exciting light is irradiated from the endoscope 2 toward the living tissue of the observation object, and fluorescence is emitted from the living tissue to which the exciting light has been irradiated. The observation image by this fluorescence is emanated from the endoscope 2 through an objective optical system 18, the image guide fiber 19 and the eyepiece optical system 20. Composition of fluorescence is extracted by the absorption filter 41, and an image of the observation image emanated from the endoscope 2 is formed on the image pick-up surface of CCD43 by an image forming optical system 42. Thereby, an image of photographing object by the fluorescence is displayed on a monitoring equipment 6.

At this time, in many cases, a portion emitting fluorescence is a small area in the whole observation portion by the endoscope 2. Therefore, there is a case that a position where the portion emitting fluorescence is located in the whole observation portion cannot be identified. In such case, the whole observation portion can be observed by such a way that an excitation filter 33 is retracted out of the illumination light path, and visible light including a transmitted wavelength of the absorption filter 41 is irradiated toward an organization for observation.

Here, the living tissue of the observation object is not limited to only the tissue and the cell of a human or an animal, but it can be a tissue and a cell of other living creature.

FIG. 2 is a graph showing a spectrum characteristic of the relation between a wavelength and a transmittance of a filter which is used for the endoscope for medical application of the first embodiment, where a characteristic curve D shows a transmittance characteristic of the excitation filter 33, and a characteristic curve E shows the transmittance characteristic of the absorption filter 41, respectively.

A half-value wavelength at a long-wavelength side of the excitation filter 33 is 489.5 nm and a half-value wavelength at a short-wavelength side of the absorption filter 41 is 494 nm, and an interval of them, that is, a wavelength width is 4.5 nm.

A half-value wavelength at a short-wavelength side of the excitation filter 33 is 469.5 nm, and a half-value wavelength at a long wave side of the absorption filter 41 is 542.7 nm.

Characteristics of each filter will be explained in detail, based on the graph (characteristic diagram) of FIG. 2. The excitation filter 33 has a characteristic such that the range of a half-value wavelength where a transmittance becomes a half of the maximum value (50%) is 469.5~489.5 nm and the wavelength range where a transmittance becomes 0.1% or less is 300~459.7 nm and 490.7~1000 nm, and the wavelength range where a transmittance becomes 80% or more is 471.3~489.2 nm.

On the other hand, the absorption filter 41 has a characteristic such that a range of a half-value wavelength where a transmittance becomes a half of the maximum value (50%) is 497.05~542.7 nm and a wavelength range where a transmittance becomes 0.1% or less is 384.0~492.8 nm and 547.8~840 nm, and a wavelength range where a transmittance becomes 80% or more is 494.1~543.0 nm.

In the characteristic diagram of each of filters 33 and 41, a distinction between the line of characteristic where a transmittance becomes 0.1% or less and the line where a transmittance is 0% cannot be identified. According to the first embodiment, the interval of the half-value wavelength at a long wave side of an excitation filter 33 and the half-value wavelength at a short-wavelength side of the absorption filter 41 is narrow, and an area of no use decreases. Therefore, fluorescence can be efficiently generated from a living tissue, and it can be observed efficiently.

Although these filters are shown in FIGS. 1 and 2, as if these were composed of single sheet, respectively, in fact these are composed by combining several sheets of filter. Concretely, the excitation filter 33 having characteristic curve D, determines an optical characteristic of the exciting light which is irradiated to a living tissue are determined, by two combinations of the long wave pass (LWP) filter H which has an optical characteristic and the short wave pass (SWP) filter G as shown in FIG. 3, and furthermore, it contains filters I, J, and K which cut off unnecessary ultraviolet light and infrared light when it is irradiated to a living tissue as shown in FIG. 4.

Figure 4:
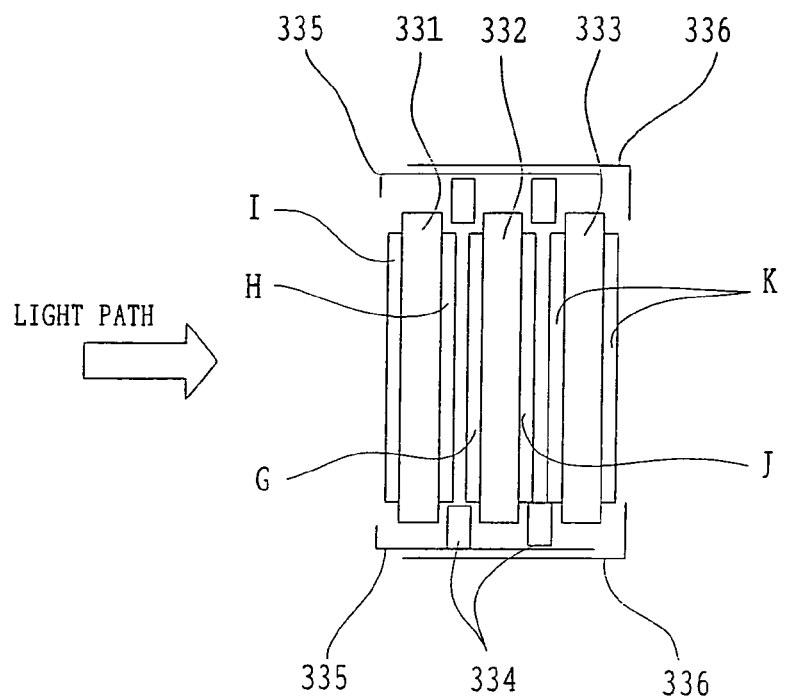
FIG. 4 is a sectional diagram showing a composition of the excitation filter shown in FIGS. 1 and 2.

FIG. 4 is a sectional diagram showing a composition of the excitation filter 33. In filters composing the excitation filter 33 shown in FIG. 4, SWP filter G having the largest effect to fluorescence observation performance is constructed such that it has 126 layers composition in which film of $SiO_2$ (refractive index at wavelength of 450~550 nm is 1.46~1.47) and $Ta_2O_5$ (refractive index at wavelength of 450~550 nm is 2.19~2.25) used as a low refractive index film and a high refractive index film are alternately laminated on the substrate 332, and it is formed by the ion plating method of RF applied system. This SWP filter G is used in the excitation filter 33 as a filter for determining the long-wavelength side of the wavelength band of the exciting light. This SWP filter G is a filter which makes transmittance of the exciting light 0.1% or less at a longer wavelength side (range of 490.7~627.0 nm) than a wavelength at the long-wavelength side which has been determined as mentioned above (the half-value wavelength is 489.5 nm and a wavelength at 80% of transmittance is 489.2 nm).

Similarly, LWP filter H has 54 layers composition in which film of $SiO_2$ and $Ta_2O_5$ are alternately laminated on the substrate 331, and it is formed by the ion plating method of RF applying system. This LWP filter H is used in the excitation filter 33 as a filter for determining a short-wavelength side of the wavelength band of the exciting light. This LWP filter H is a filter which makes transmittance of the exciting light 0.1% or less at a shorter wavelength side (range of 367.0~459.7 nm) than a wavelength at the short-wavelength side which has been determined as above-mentioned (a half-value wavelength is 469.5 nm and a wavelength at 80% of transmittance is 471.3 nm).

A filter I for cutting ultraviolet light, and filters J and K for cutting infrared light are used in order to expand further a cutoff range (range where light having a wavelength which is not used for fluorescence observation does not transmit) by filters G and H. As for these filters I, J, and K, even if an optical characteristic is shifted within a scope in which optical characteristic overlaps cutoff bands of filters G and H by humidity change, there is no influence to a transmission band of the wavelength of the exciting light for carrying out fluorescence observation. As for these filters I, J, and K, it has composition in which a film of $SiO_2$ (refractive index at wavelength of 400~1000 nm is 1.45~1.47) and $Ta_2O_5$ (refractive index at wavelength of 400~1000 nm is 2.24~2.58) used are alternately laminated on the substrates 331, 332 and 333 by vacuum evaporation method, respectively, and the filter I and the filter J are formed by 40 layers, and the filter K is formed by 46 layers.

Film composition of each of filters I, H, G, J, and K composing this excitation filter 33 is shown in Table 1.

In film composition, λ/4 in term of an optical thickness of film is set to 1.0, and it is shown in order from a substrate side to an air space side. In the table 1, $Ta_2O_5$ is set to H, and $SiO_2$ is set to L in the film composition of filters H and G and H. $TiO_2$ is set to H and $SiO_2$ is set to L in the film composition of filters I, J, and K. Optical glass BK7 is used for the substrates 331,332 and 333. As shown in FIG. 4, it is constructed such that the substrates 331,332 and 333 are arranged in order from the entrance side of light (optical path) on the excitation filter 33, wherein the filter I is at the entrance side of the substrate 331, the filter H is at the exit side, the filter G is at the entrance side of the substrate 332, the filter J is at the exit side, and the filter K is at both of the entrance sides and the exit sides of the substrate 333.

TABLE 1

| | Filter | Layer | λ | Film composition: from substrate side to air space side |
|---|---|---|---|---|
| Excitation Filter | I | 40 Layers | 365 nm | .4717H .8376L .9153H .8793L .877H 1.0091L .8576H .9991L .8887H 1.0232L .886H 1.014L .8922H 1.0237L .8876H 1.0155L .8893H 1.0257L .8982H 1.0224L .8956H 1.0322L .8956H 1.0027L .8765H 1.0474L .921H 1.0026L .8655H 1.0313L .9293H .9546L .9049H 1.0343L .9088H .8934L 1.0019H .7406L .9492H 1.7252L |
| | H | 54 Layers | 512 nm | .7402H .2246L .5191H 1.5504L 1.1453H .5478L .6848H .6556L .7053H .7767L .857H .8891L .8515H .6819L .5828H .9274L .7852H .7995L .7907H .7973L .7752H .7906L .7781H .7897L .7744H .8002L .7763H .7891L .7741H .7983L .7914H .8038L .7841H .8006L .7934H .7843L .7566H .7731L .7722H .7973L .7881H .8127L .8117H .7858L .7947H .7813L .5139H .7856L 1.0456H .9833L .6587H .4989L .7024H 1.584L |
| | G | 126 Layers | 562 nm | .4129H 1.8825L .2515H 1.1383L 1.1756H .9966L .8251H 1.0511L 1.1333H 1.0346L .883H .8834L .1.0202H 1.0063L 1.0061L 1.0011L .994H .9758L .9597H .9585L .9896H .9882L .988H .9791L .9945H .9808L .9821H .9676L .9709H .9751L .9855H .9843L .9916H .9815L .9816H .9756L .9681H .9682L .982H .989L .9869H .981L .9787H .9763L .9775H .9725L .9756H .9788L .9875H .9843L .9813H .9765L .9752H .9736L .9764H .9781L .9859H .9873L .9827H .9746L .97H .9705L .9786H .983L .9853H .9825L .9827H .9768L .977H .9738L .978H .976L .9811H .977L .9838H .983L .9867H .9765L .9717H .9669L .9735H .9774L .1.0066H .9729L .9746H .9775L .9788H .9773L .9785H .9838L .985H .9781L .9698H .969L .99H .9903L .9927H .975L .927H .997L 1.0023H .9923L .9791H .9746L .9738H .9669L .9612H .9769L 1.04H .9833L .9917H .9386L .9565H .9997L 1.0011H .9861L .9959H 1.0112L .9943H .9635L .9787H 1.035L 1.056H 1.0468L .9806H .5042L |
| | J | 40 Layers | 630 nm | .104H .3641L 1.5729H .384L 1.5215H .6875L 1.282H .8823L 1.0826H 1.0057L 1.0206H .9786L 1.0308H .9762L 1.0251H .9748L 1.0268H .9744L 1.0243H .9731L 1.0248H .9728L 1.0228H .9715L 1.0238H .9738L 1.0243H .9731L 1.0266H .9794L 1.0311H .9817L 1.0349H .9883L 1.0527H .9913L 1.076H 1.0609L 1.0426H .5398L |
| | K | 46 Layers | 730 nm | .1138H .2469L 1.421H .1998L 1.3338H 1.0436L 1.0357H .9602L 1.0141H .9759L .978H 1.0107L .962H 1.0081L .9867H .9955L 1.0037H .9949L 1.0263H 1.0164L 1.039H 1.0074L 1.0086H 1.1092L 1.1082H 1.2087L 1.2397H 1.4037L 1.2535H 1.2343L 1.1688H 1.2798L 1.2738H 1.3348L 1.2873H 1.3122L 1.2015H 1.2358L 1.2137H 1.353L 1.353H 1.4123L 1.4016H 1.3646L 1.1353H .5852L |
| Absorption Filter | L | 148 Layers | 441 nm | .1635H 1.7085L .4484H .9814L .9552H .904L .785H 1.0077L 1.0924H 1.018L .8801H .8507L .9695H .9719L .9872H .975L .9584H .9404L .9346H .9333L .942H .9475L .9574H .9524L .9653H .9465L .9496H .9435L .9506H .9519L .963H .9685L .9741H .9706L .9658H .9571L .9538H .9529L .9575H .9604L .9645H .9621L .9595H .9505L .9459H .9373L .9398H .9444L .9534H .9534L .9525H .9466L .947H .9478L .9543H .961L .9683H .9718L .9731H .9728L .9724H .9725L .9731H .9738L .975H .9754L .978H .9889L .9838H .9826L .9835H .977L .9778H .9742L .9803H .9814L .9885H .9869L .9869H .9783L .9745H .9711L .9995H .9733L .9779H .9829L .9883H .9902L .9889H .9834L .9768H .9711L .9713H .9772L .9906H 1.0026L 1.0082H .9876L .9282H .9849L .9872H .9867L .9859H .9847L .9834H .9824L .9819H .982L 1.0101H .9445L .9845H .985L .985H .9843L .9832H .9818L .9807H .98L .98H .98L .981H .9816L .9816H .981L .9797H .9782L .9769H .976L .977H .979L .9822H .9854L .9874H .987L .8849H .9338L .975H 1.1998L 1.1464H .5093L 1.0826H .9426L 1.31H .7273L .8909H .7762L .9948H 1.6256L |
| | M | 90 | 604 nm | .2775H 1.5503L 1.0703H 1.0726L .9993H 1.1179L 1.0027H 1.0121L 1.02H 1.0214L |

TABLE 1-continued

| Filter | Layer | λ | Film composition: from substrate side to air space side |
|---|---|---|---|
| | Layers | | 1.0262H 1.0129L 1.0106H 1.0153L 1.0177H 1.0175L 1.0098H 1.0072L 1.009H 1.0155L |
| | | | 1.0166H 1.0129L 1.007H 1.0076L 1.0106H 1.0145L 1.0131H 1.0101L 1.0075H 1.0097L |
| | | | 1.012H 1.0131L 1.0102H 1.0091L 1.009H 1.0116L 1.0123H 1.0119L 1.0094H 1.01L |
| | | | 1.0106H 1.0128L 1.0121H 1.0128L 1.0126H 1.0142L 1.0113H 1.0053L 1.0522H 1.0035L |
| | | | .9981H 1.04L 1.1189H .9539L 1.1072H 1.1909L 1.1473H 1.3243L 1.2349H 1.2112L |
| | | | 1.2337H 1.2739L 1.337H 1.2942L 1.2161H 1.251L 1.2768H 1.376L 1.268H 1.2399L |
| | | | 1.2147H 1.292L 1.3709H 1.304L 1.2415H 1.2255L 1.2774H 1.3699L 1.2765H 1.2549L |
| | | | 1.2012H 1.2868L 1.3763H 1.2818L 1.2507H 1.1177L 1.1156H 1.2743L .9869H .6999L |

Figure 5:
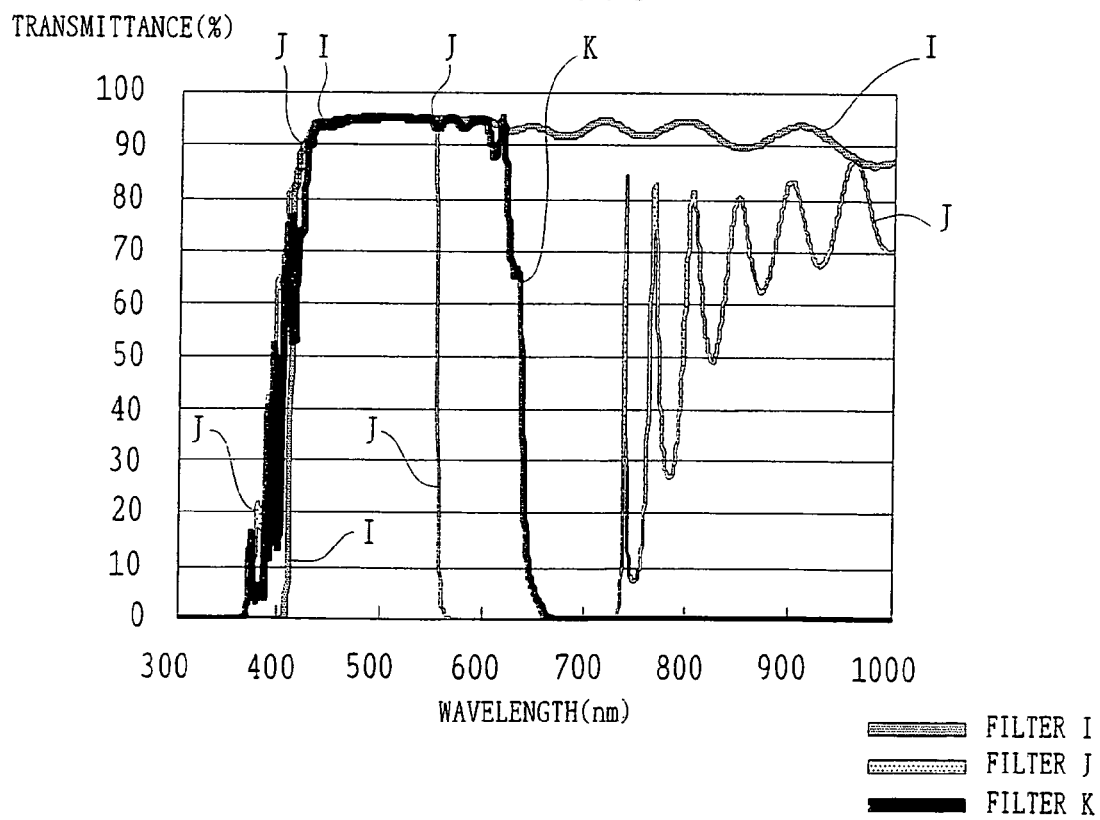
FIG. 5 is a graph showing optical characteristics of each filter which constitutes the excitation filter shown in FIGS. 1 and 2.

Optical characteristics of wavelength range from 300 nm to 1000 m about filters G and H are shown in FIG. 3. Optical characteristics from 300 nm to 1000 m of wavelength ranges about filters I, J and K are shown in FIG. 5. In each of filters G, H, I, J, and K, each transmittance is made 0.1% or less in the wavelength range of Table 2 and accordingly a wavelength except the transmission band of the exciting light is cut.

TABLE 2

| | I | H | G | J | K |
|---|---|---|---|---|---|
| Cutoff range | 300-400 nm | 367-459 nm | 491-627 nm | 568-724 nm | 685-1000 nm |

Similar to case of the excitation filter 33, the absorption filter 41 can be composed of a LWP filter, a SWP filter and a filter that cuts off unnecessary light. In this case, if generated fluorescence which is unnecessary for observation is cut off by the LWP filter and the SWP filter which constitute an absorption filter, a filter for cutting off unnecessary light is not particularly needed.

Figure 6:
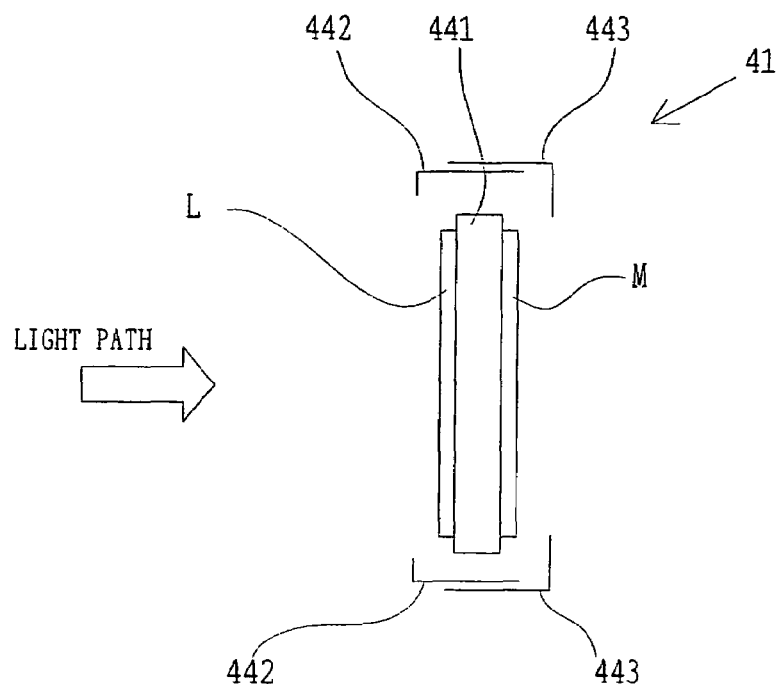
FIG. 6 is a sectional diagram showing a composition of an absorption filter shown in FIGS. 1 and 2.

FIG. 6 shows an outline composition of the absorption filter 41 of the first embodiment.

In the first embodiment, as shown in FIG. 6, the absorption filter 41 having characteristic curve E shown in FIG. 2 has the LWP filter L and the SWP filter M on both sides of the substrate 441 respectively, and it is constructed so that all unnecessary fluorescence for observation can be cut off by the SWP filter M. For this, it is not necessary to increase the number of filter for cutting the unnecessary light.

In the absorption filter 41, the substrate 441 is sandwiched by the inner frame 442 and the outer frame 443 from the both sides.

Optical glass BK7 is used for the substrate 441. The film configuration of each of filters L and M is shown in the table 1. In film composition, λ/4 in term of an optical thickness of film is set to 1.0, and it is shown in order from the substrate side to an air space side. The LWP filter L which has the largest influence to a fluorescence observation performance is formed by the ion plating method of RF applying system, wherein the films of $SiO_2$ and $Ta_2O_5$ is laminated alternately, and it has 148 layers.

Figure 7:
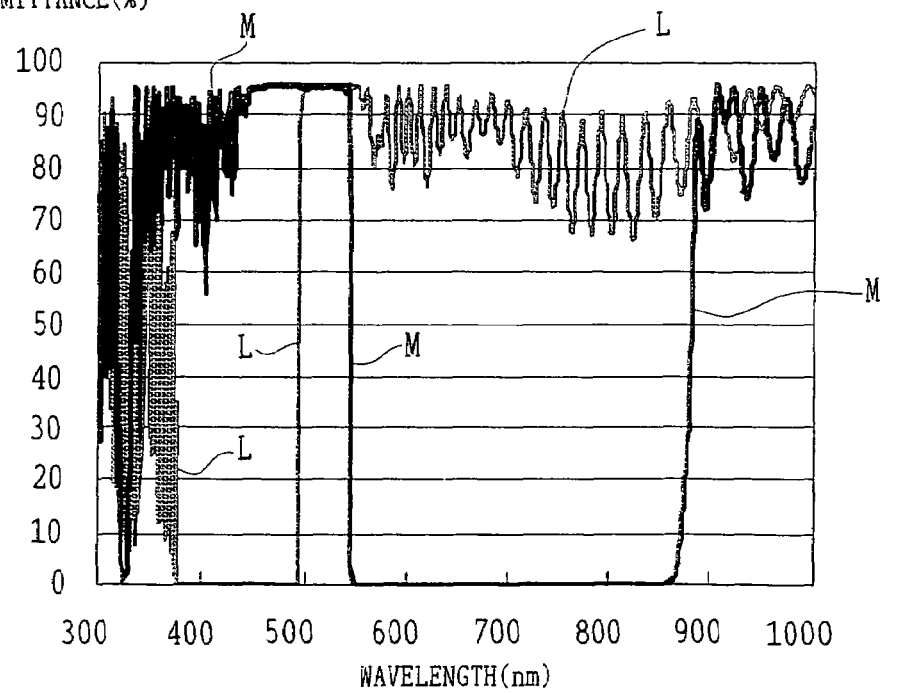
FIG. 7 is a graph showing transmittance characteristics of a long wave pass filter and a short wave pass filter which constitute the absorption filter shown in FIGS. 1 and 2.

Similarly, SWP filter M has 90 layers composition in which the film of $SiO_2$ and $Ta_2O_5$ are alternately laminated, and it is formed by the ion plating method of RF applying system. Optical characteristics from 300 nm to 1000 nm of wavelength ranges about filters L and M are shown in FIG. 7. In the table 1, in the film composition of filters L and M, $Ta_2O_5$ is shown as H and $SiO_2$ is shown as L.

In FIG. 7, the LWP filter L is used in the absorption filter 41 as a filter for determining a short-wavelength side of the wavelength band of the fluorescence for observation. This LWP filter L is a filter which makes a transmittance of the fluorescence 0.1% or less at a shorter wavelength side (range from 348.0 to 492.8) than a wavelength (wavelength is 494.0 when a half-wavelength is 494.0 nm and transmittance is 80%) at the short-wavelength side which has been determined as mentioned above.

This SWP filter M is used in the absorption filter 41 as a filter for determining the short-wavelength side of the wavelength band of of the fluorescence for observation. This SWP filter M is a filter which makes transmittance of the fluorescence 0.1% or less at a longer wavelength side (range of 547.8~840.0 nm) than a wavelength (wavelength is 543.0 when a half-wavelength is 542.7 nm and transmittance is 80%) at the long-wavelength side which has been determined as mentioned above. Therefore, in the LWP filter L and the SWP filter M of an absorption filter 41, each transmittance is made 0.1% or less in the wavelength range of the Table 3 and wavelength except the transmission band of the fluorescence for observation is cut.

TABLE 3

| | L | M |
|---|---|---|
| Cutoff range | 384.0-492.8 nm | 547.8-840.0 nm |

Therefore, the observation is carried out by setting the wavelength range of the fluorescence used for observation 492.8 nm~547.8 nm. As for optical characteristics of filters H, G, L and M formed by the ion plating method of RF applying system, change of the half-value wavelength is 0~+0.1 nm when humidity changes from 10% to 95%, and both are 0.5 nm or less.

Evaluation of optical characteristics has been carried out concretely by the following test condition.

A substrate of BK7 where a film is formed only on one side on the substrate by each of filters H, G, L, and M formed by the ion plating method of RF applying system, the excitation filter 33 and the absorption filter 41 are prepared, respectively.

After the substrate having a formed film of filters H, G, L, and M the excitation filter 33 and the absorption filter 41 were exposed for four days under an environment kept at 10% of humidity in normal temperature (20 degrees C.) in a container in which these things mentioned above and silica gel are reserved, these were put in a constant temperature-humidity bath at 20° C. and 95% for 100 hours. Then, change of a spectrum characteristic was investigated before and behind the test. The change of the half-value wavelength before and after the test is shown in Table 4.

TABLE 4

|  | Filter H | Filter G | Filter L | Filter M | Excitation Filter Short wavelength side | Excitation Filter Long wavelength side | Absorption Filter Short avelength side | Absorption Filter Long wavelength side |
|---|---|---|---|---|---|---|---|---|
| Before | 469.5 | 489.5 | 494 | 542.7 | 469.5 | 489.5 | 494 | 542.7 |
| After | 469.5 | 489.5 | 494 | 542.8 | 469.5 | 489.5 | 494 | 542.8 |
| Amount of change | 0.0 | 0.0 | 0.0 | 0.1 | 0.0 | 0.0 | 0.0 | 0.1 | unit: nm

A living tissue was observed using the endoscope of the first embodiment constructed in this way mentioned above. Since observation can be carried out by picking up fluorescence very efficiently, even if an illumination light was weakened, the observation was able to be sufficiently carried out. Therefore, the living tissue was not deteriorated.

The wavelength interval which is an interval between the half-value wavelength at the long wave side of SWP filter G of the excitation filter 33 and the half-value wavelength at the short-wavelength side of LWP filter L of the absorption filter 41 was 4.5 nm. By shifting the characteristics of filters G and L, that is, the excitation filter 33 and the absorption filter 41, the living tissue could be observed at bright state in any case that the wavelength width was 1~6 nm without a big difference in the result of possible observation In case that filters H, G, L, and M which were formed by the ion assist method, the sputtering method, or the ion beam sputtering method were used instead of using what were formed by the ion plating method of RF applying system, the same result was obtained. When $Nb_2O_5$, $TiO_2$, or one of mixtures of these was used by replacing $Ta_2O_5$ for forming the film, the film composition of filters changed, but the same result was obtained.

In an example shown in FIG. 4 or FIG. 6, in the first embodiment, although optical glass of BK7 was used for the substrate of the excitation filter 33 and the absorption filter 41, an absorption glass having capability to absorb an ultraviolet ray and to cut off the exciting light or fluorescence in an unnecessary wavelength band, and a colored glass which absorbs visible ray can be used in place of an optical glass. In such case, efficiency of light cutting can be improved without any problem for observation.

Second Embodiment

Figure 8:
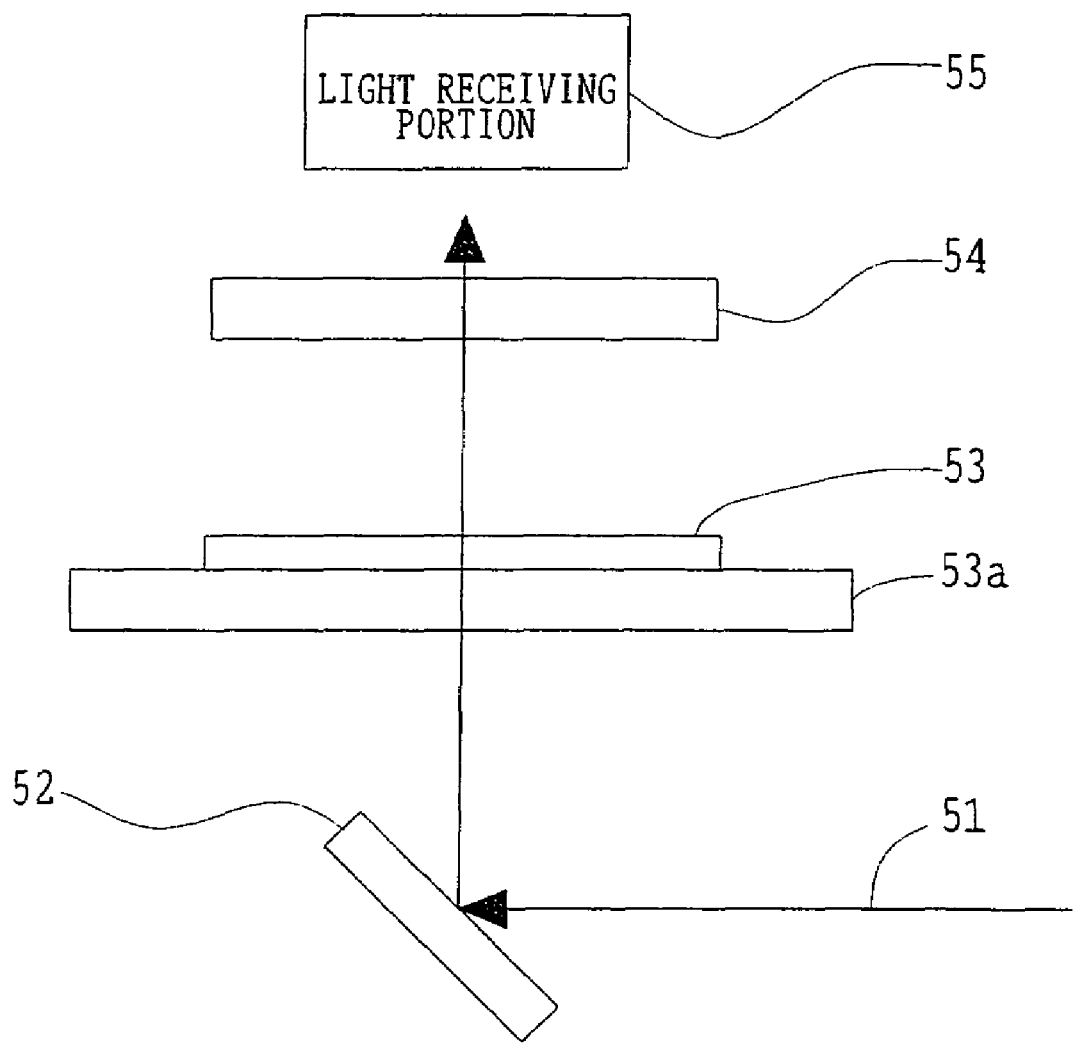
FIG. 8 is an outline composition diagram of an optical system of a fluorescence intensity measuring instrument concerning the second embodiment of the apparatus for fluorescence observation according to the present invention.

FIG. 8 is an outline composition diagram of an optical system of a fluorescence intensity measuring instrument concerning the second embodiment of the apparatus for fluorescence observation according to the present invention.

In the optical system shown in FIG. 8, an optical path of laser light 51 having wavelength of 488 nm and intensity of 800 mW which is emanated from a laser source that is not illustrated, is bent as exciting light by the mirror 52, and then it is irradiated to the specimen 53 on a specimen installation stand 53a. In an absorption filter 54, only the fluorescence generated from the specimen 53 transmits selectively. This system is constructed such that fluorescence can be observed by measuring the intensity of this fluorescence by CCD and a light receiving portion 55 which has a function of displaying a signal after a signal detected by CCD has been converted to an electric current value.

As for the absorption filter 54, a filter having a similar composition of the absorption filter 41 in the first embodiment is used. The wavelength of the laser light 51 having a function of exciting light is 488 nm and the half-value wavelength at the short-wavelength side of the absorption filter 54 is 494 nm, and a wavelength width which is an interval between the half-value wavelength at the wavelength of the laser light 51 and the short-wavelength side of the absorption filter 54 is 6 nm. By this composition, fluorescence generated from the specimen 53 can be picked up efficiently, and measurement in high sensitivity state can be carried out at a light receiving portion 55. As for this interval (wavelength width), by shifting the characteristic of the absorption filter 54, namely, by changing a film composition so that the half-value wavelength at the short-wavelength side in the spectrum transmittance characteristic of the absorption filter 54 is brought close to the wavelength side of the laser light 51, or it is departed away from the wavelength side of the laser light 51, measurement with high sensitivity was achieved in both cases, even if it was changed from 1 nm to 12 nm.

However, if the interval is from 1 nm to 5 nm, even the laser light having the wavelength range which is not to transmit the absorption filter 54 cannot be cut off, depending upon an irradiation intensity of the laser light 51, and a condition of the irradiation time to the specimen 53. Accordingly, there is a possibility that the laser light 51 may leak to a light receiving portion 55. In that case, by taking measures for weakening an intensity of the laser light 51, or for decreasing the time to irradiate the laser light 51 to the specimen 53, an unfavorable influence by the laser light 51 can be suppressed when a fluorescence observation is carried out. It is desirable that an interval (wavelength width) between a wavelength of the laser light 51 and a half-value wavelength at the short-wavelength side of the absorption filter 54 is set 6 nm to 12 nm.

The similar result has been obtained in case that LWP filter L and SWP filter M which compose the absorption filter 54 formed by the ion plating method of RF applying system, is formed by the ion assist method or the ion beam sputtering method. The effect which is similar to that of a case where a filter film thickness is formed by using the refractive index of these films has been obtained, even in a case that $Nb_2O_5$, TiO₂, or the mixture of one of these is used in stead of Ta₂O₅ for forming the film of the filter L and the filter M.

Third Embodiment

The excitation filter 33 and the absorption filter 41 in the first embodiment were replaced by a filter which has a characteristic shown in a graph showing a relation between the wavelength and the transmittance of the filter in FIG. 9.

A half-value wavelength at a long-wavelength side of the excited filter 33 is 459.5 nm and a half-value wavelength at a short-wavelength side of the absorption filter 41 is 462.8, and the wavelength width which is an interval of these is 3.3 nm.

Characteristic of each filter will be explained more in detail based on the graph (characteristic diagram) of FIG. 9. The excitation filter 33 has a transmittance characteristic such that the range of the half-value wavelength where a transmittance becomes as a half of the maximum value (50%) is 433.4~459.5 nm and the wavelength range where a transmittance becomes 0.1% or less is 300 nm~421.1 nm and 460.4 nm~1000 nm, and a wavelength range where a transmittance becomes 80% or more is 435.7 nm~459.3 nm.

It becomes impossible to distinguish a line of characteristic where the transmittance becomes 0.1% or less, and a line where transmittance is 0%. On the other hand, a range of the half-value wavelength where the transmittance becomes as a half of the maximum value (50%) is 462.8~487.6 nm and the wavelength range where the transmittance becomes 0.1% or less is 334 nm~461.17 nm and 494.2 nm~810 nm, and a wavelength range where the transmittance becomes 80% or more is 463.2 nm~486.4 nm. It becomes impossible to distinguish the line of characteristics where transmittance becomes 0.1% or less, and the line where transmittance is 0%.

As filters I, J, and K for cutting an unnecessary ultraviolet ray and infrared light among filters I, H, G, J, and K composing the excitation filter 33, filters having the film forming material and the film characteristics which are used in the first embodiment have been used. Characteristics of LWP filter H and SWP filter G are shown in FIG. 10.

SWP filter G having the largest influence to fluorescence observation performance has 126 layers composition in which a film of SiO₂ (refractive index at wavelength of 450~650 nm is 1.46~1.47) and a film of TiO₂ (refractive index at wavelength of 400~650 nm is 2.45~2.61) are alternately laminated on the substrate, and it is formed by the ion assist method using an ion gun.

LWP filter H is composed of 32 layers composition in which a film of SiO₂ (refractive index at wavelength of 400~650 nm is 1.46-1.47) and TiO₂ (refractive index at wavelength of 400~650 nm is 2.45-2.61) are alternately laminated on the substrate, by the ion assist method using the ion gun.

The film compositions are shown in Table 5.

TABLE 5

| | Filter | Layer | λ | Film composition: from substrate side to air space side |
|---|---|---|---|---|
| Excitation Filter | I | 40 Layers | 365 nm | .4717H .8376L .9153H .8793L .877H 1.0091L .8576H .9991L .8887H 1.0232L .886H 1.014L .8922H 1.0237L .8876H 1.0155L .8893H 1.0257L .8982H 1.0224L .8956H 1.0822L .8956H 1.0027L .8765H 1.0474L .921H 1.0026L .8655H 1.0313L .9293H .9546L .9049H 1.0343L .9088H .8934L 1.0019H .7405L .9492H 1.7252L |
| | H | 32 Layers | 446 nm | .4636H .5368L .87H .7643L .6606H .8102L .7366H .8177L .7406H .8178L .738H .8172L .7425H .8222L .7451H .8248L .7465H .8236L .7434H .8205L .7412H .8216L .7443H .8218L .7403H .8174L .7392H .7664L .6448H .8143L .6443H 1.435L |
| | G | 126 Layers | 541 nm | .4129H 1.8825L .2515H 1.1383L 1.1756H .9966L .8251H 1.0511L 1.1333H 1.0346L .883H .8834L 1.0202H 1.0063L 1.0061H 1.0011L .994H .9758L .9597H .9585L .9896H .9882L .988H .9791L .9945H .9808L .9821H .9676L .9709H .9751L .9855H .9843L .9916H .9815L .9816H .9756L .9681H .9682L .982H .989L .9869H .981L .9787H .9763L .9775H .9725L .9756H .9788L .9875H .9843L .9813H .9765L .9752H .9736L .9764H .9781L .9859H .9873L .9827H .9746L .97H .9705L .9786H .983L .9853H .9825L .9827H .9768L .977H .9738L .978H .976L .9811H .977L .9838H .983L .9867H .9765L .9717H .9669L .9735H .9774L 1.0066H .9729L .9746H .9775L .9788H .9773L .9785H .9838L .985H .9781L .9698H .969L .99H .9903L .9927H .975L .927H .997L 1.0023H .9923L .9791H .9746L .9738H .9669L .9612H .9769L 1.04H .9833L .9917H .9386L .9565H .9997L 1.0011H .9861L .9959H 1.0112L .9943H .9635L .9787H 1.035L 1.056H 1.0468L .9805H .5042L |
| | J | 40 Layers | 630 nm | .104H .3641L 1.5729H .384L 1.5215H .6875L 1.282H .8823L 1.0826H 1.0057L 1.0206H .9786L 1.0308H .9762L 1.0251H .9748L 1.0268H .9744L 1.0243H .9731L 1.0248H .9728L 1.0228H .9715L 1.0238H .9738L 1.0243H .9731L 1.0266H .9794L 1.0311H .9817L 1.0349H .9883L 1.0527H .9913L 1.076H 1.0609L 1.0426H .5398L |
| | K | 46 Layers | 730 nm | .1138H .2469L 1.421H .1998L 1.3338H 1.0436L 1.0357H .9602L 1.0141H .9759L .978H 1.0107L .962H 1.0081L .9867H .9955L 1.0037H .9949L 1.0263H 1.0164L 1.039H 1.0074L 1.0086H 1.1092L 1.1082H 1.2087L 1.2397H 1.4037L 1.2535H 1.2343L 1.1688H 1.2798L 1.2738H 1.3348L 1.2873H 1.3122L 1.2015H 1.2358L 1.2137H 1.353L 1.353H 1.4123L 1.4016H 1.3646L 1.1353H .5852L |
| Absorption Filter | L | 148 Layers | 400 nm | .1635H 1.7085L .4484H .9814L .9552H .904L .785H 1.0077L 1.0924H 1.0178L .8801H .8507L .9695H .9719L .9872H .9752L .9584H .9404L .9346H .9333L .942H .9475L .9574H .9524L .9653H .9465L .9496H .9435L .9505H .9519L .963H .9685L .9741H .9706L .9658H .9571L .9538H .9529L .9575H .9604L .9645H .9621L .9595H .9505L .9459H .9373L .9398H .9444L .9534H .9534L .9525H .9466L .947H .9478L .9543H .961L .9683H .9718L .9731H .9728L .9724H .9725L .9731H .9738L .975H .9754L .978H .989L .9838H .9826L .9835H .977L .9778H .9742L .9803H .9814L .9885H .9869L .9869H .9783L .9745H .9711L .9995H .9733L .9779H .9829L .9883H .9902L .9889H .9834L .9768H .9711L .9713H .9772L .9906H 1.0026L 1.0082H .9876L .9282H .9849L .9872H .9867L .9859H .9847L .9834H .9824L .9819H .982L 1.0101H .9445L .9845H .985L .985H .9843L .9832H .9818L .9807H .98L .9799H .9803L .981H .9816L .9816H .981L .9797H .9782L .9769H .9764L .977H .979L |

TABLE 5-continued

| Filter | Layer | λ | Film composition: from substrate side to air space side |
|---|---|---|---|
| M | 80 Layers | 558 nm | .9822H .9854L .9874H .987L .8849H .9338L .9751H 1.1998L 1.1464H .5093L 1.0826H .9426L 1.31H .7273L .8909H .7762L .9948H 1.6256L .2775H 1.5503L 1.0703H 1.0726L .9993H 1.1179L 1.0027H 1.0121L 1.02H 1.0214L 1.0262H 1.0129L 1.0106H 1.0153L 1.0177H 1.0175L 1.0098H 1.0072L 1.0075H 1.0097L 1.012H 1.0131L 1.0102H 1.0091L 1.009H 1.0116L 1.0123H 1.0119L 1.009H 1.01L 1.0106H 1.0128L 1.0121H 1.0128L 1.0126H 1.0142L 1.0113H 1.0053L 1.0522H 1.0035L .9981H 1.04L 1.1189H .9539L 1.1072H 1.1909L 1.1473H 1.3243L 1.2349H 1.2112L 1.2337H 1.2739L 1.337H 1.2942L 1.2161H 1.251L 1.2768H 1.376L 1.268H 1.2399L 1.2147H 1.292L 1.3709H 1.304L 1.2415H 1.2255L 1.2774H 1.3699L 1.2765H 1.2549L 1.2012H 1.2868L 1.3763H 1.2818L 1.2507H 1.1177L 1.1156H 1.2743L .9869H .6999L |

In the table 5, $TiO_2$ is set to H, and $SiO_2$ is set to L in the film composition of filters G and H. $TiO_2$ is set to H and $SiO_2$ is set to L in the film composition of filters I, J and K.

Figure 11:
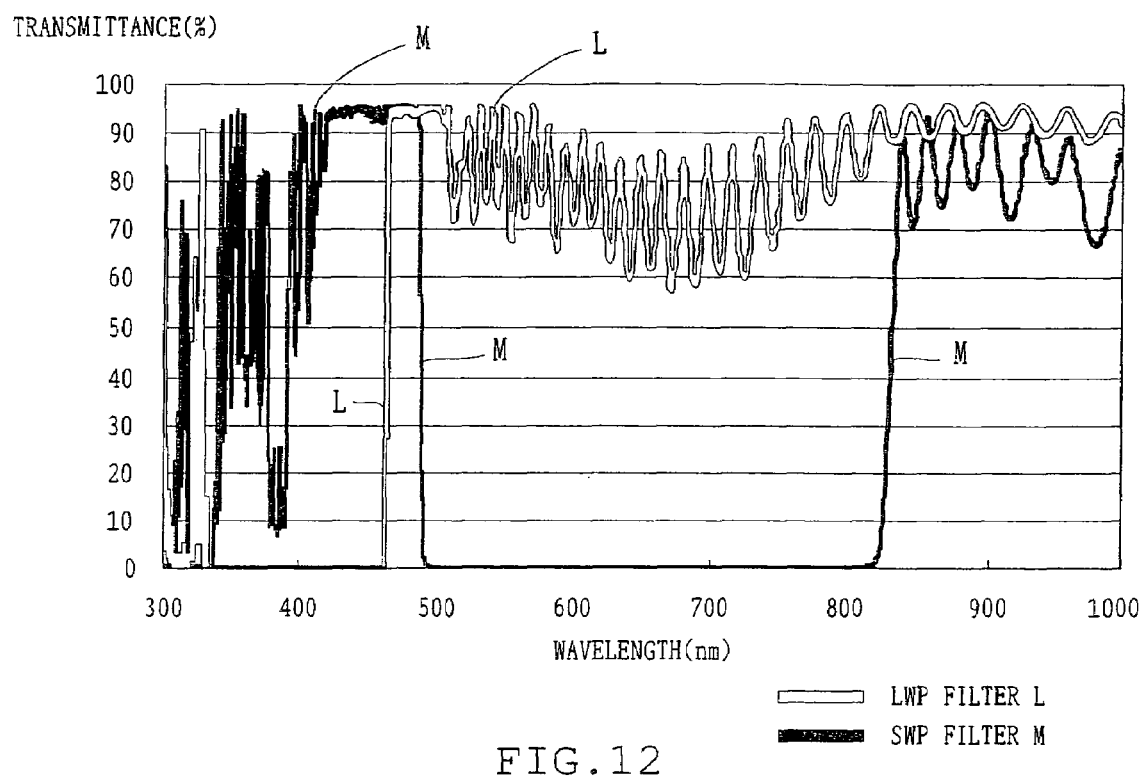
FIG. 11 is a graph showing optical characteristics of a long wave pass filter and a short wave pass filter which constitute the absorption filter shown in FIG. 9.

The absorption filter 41 is composed of filters L and M on both sides of the substrate 441, in the same as the first embodiment. Here, LWP filter L is composed of 148 layers by the ion assist method using the ion gun. LWP filter L is also composed of 80 layers by the ion assist method using the ion gun. Optical characteristics of wavelength range from 300 nm to 1000 m about filters L and M are shown in FIG. 11.

As for optical characteristics of filters H, G, L, and M formed by the ion assist method using an ion gun, change of the half-value wavelength is 0~+0.5 nm when humidity changes from 10% to 95%, and all is 0.5 nm or less.

Concretely, a test has been carried out by the following test conditions.

A substrate where each of filters H, G, L, and M formed by the ion assist method using an ion gun are formed only on one side on the substrate of BK7 respectively, the excitation filter 33, and the absorption filter 41 are prepared.

In a container in which silica gel is put, under an environment held at 10% of humidity and normal temperature (20° C.), after the substrate formed by films of filters H, G, L, and M as a film, the excitation filter 33 and the absorption filter 41 were exposed for four days, it was held in a constant temperature-humidity bath which is at 20° C. and 95% for 100 hours. Change of a spectrum characteristic has been investigated before and after the test. Change of the half-value wavelength before and after the test is shown in Table 6.

short-wavelength side of the absorption filter 41 can be narrowed compared with that in the first embodiment, and fluorescence is efficiently generated from a living tissue, as well as the observation can be efficiently achieved.

In this embodiment, $TiO_2$ has been used. However, in case that $TiO_2$ and $Ta_2O_5$, or $Nb_2O_5$, or a mixture of one of these is used, the same effect has been obtained by composing a filter film thickness by using the refractive index of these films.

Fourth Embodiment

Figure 12:
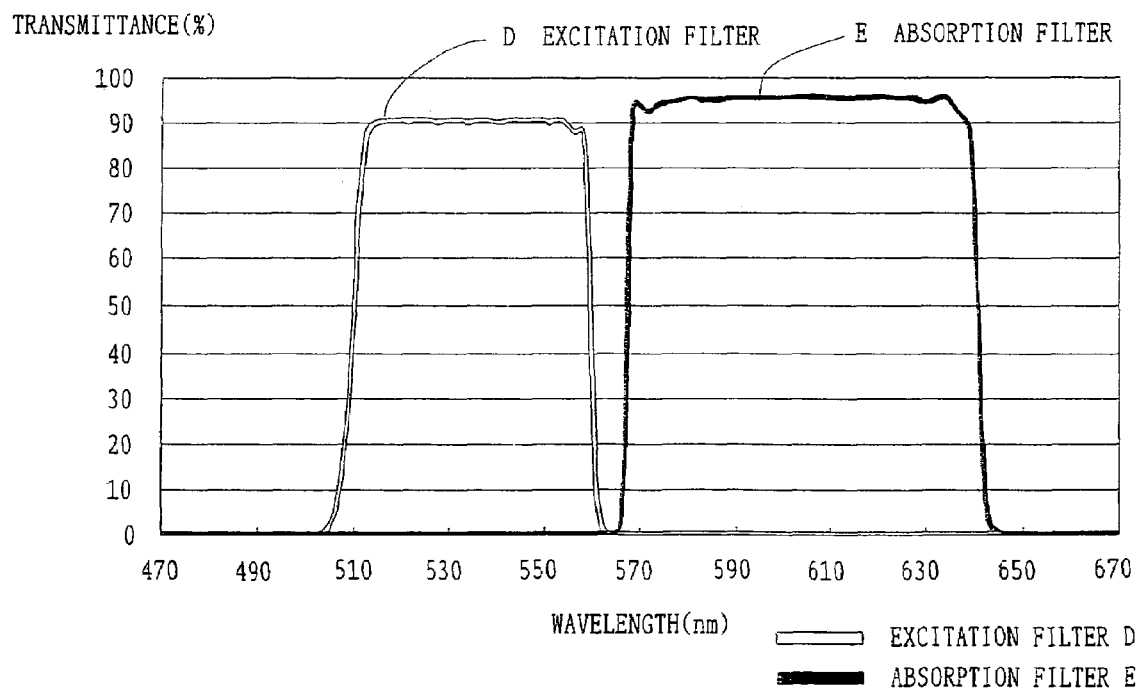
FIG. 12 is a graph showing transmittance characteristics of an excitation filter and an absorption filter used for the fourth embodiment according to the present invention.

In the fourth embodiment, the excitation filter 33 and the absorption filter 41 in the first embodiment has been replaced by a filter which has a characteristic shown in the graph showing a relation between the wavelength and the transmittance of the filter in FIG. 12.

The half-value wavelength at the long-wavelength side of the excited filter 33 is 561.5 nm and the half-value wavelength at the short-wavelength side of the absorption filter 41 is 567.5 nm and the wavelength width which is an interval of these is 6.0 nm.

Characteristics of each filter will be explained more in detail based on the graph (characteristic diagram) of FIG. 12. The excitation filter 33 has such characteristic that a range of the half-value wavelength where a transmittance becomes as a half of the maximum value (50%) is 509.7~561.5 nm and the wavelength range where a transmittance becomes 0.1% or

TABLE 6

| | | | Excitation Filter | | Absorption Filter | |
|---|---|---|---|---|---|---|
| Filter G | Filter L | Filter M | Short wavelength side | Long wavelength side | Short wavelength side | Long wavelength side |
| 459.5 | 462.8 | 487.6 | 433.4 | 459.5 | 462.8 | 487.6 |
| 459.8 | 462.8 | 488.1 | 433.4 | 459.8 | 462.8 | 488.1 |
| 0.3 | 0.0 | 0.5 | 0.0 | 0.3 | 0.0 | 0.5 | unit: nm

According to the third embodiment, by $TiO_2$ having a higher refractive index in comparison with $Ta_2O_5$ used in the first embodiment as high refractive index materials at the short-wavelength side of the absorption filter 41 and at the long-wavelength side of the excitation filter 33 having the largest influence to fluorescence observation performance, a steep characteristic can be acquired. By this, an interval between the half-value wavelength at the long wave side of the excitation filter 33 and the half-value wavelength at the less is 300 nm~500.1 nm and 562.7 nm~1000 nm, and the wavelength range where a transmittance becomes 80% is 511.2 nm~561.2 nm.

It becomes impossible to distinguish the line of characteristic where transmittance becomes 0.1% or less, and the line where transmittance is 0%.

On the other hand, a range of the half-value wavelength where a transmittance becomes as a half of the maximum value (50%) is 567.5~641.1 nm and the wavelength range where the transmittance becomes 0.1% or less is 424 nm~563.9 nm and 646.72 nm~1030 nm, and a wavelength range where the transmittance becomes 80% or more is 568.0 nm~640.1 nm.

It becomes impossible to distinguish the line of characteristic where transmittance becomes 0.1% or less, and the line where transmittance is 0%.

Figure 13:
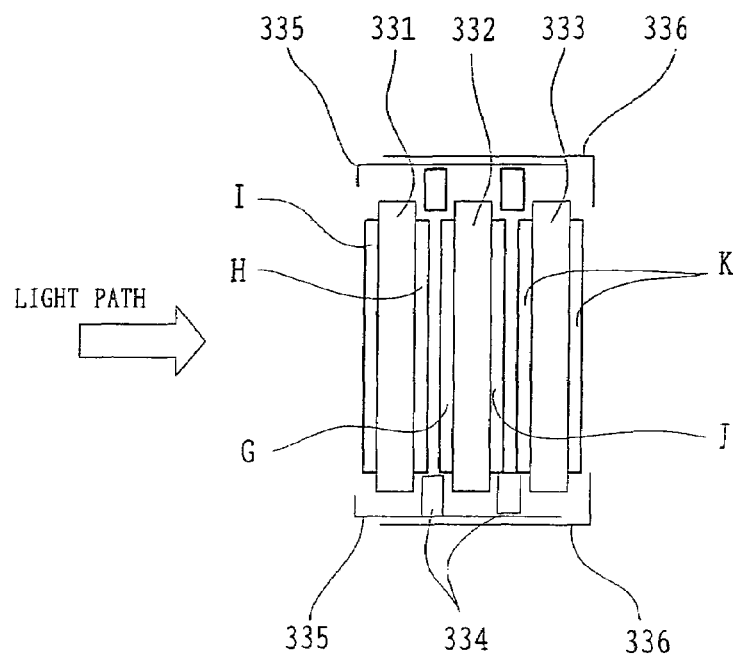
FIG. 13 is a sectional diagram showing a composition of the excitation filter used in the fourth embodiment.
Figure 14:
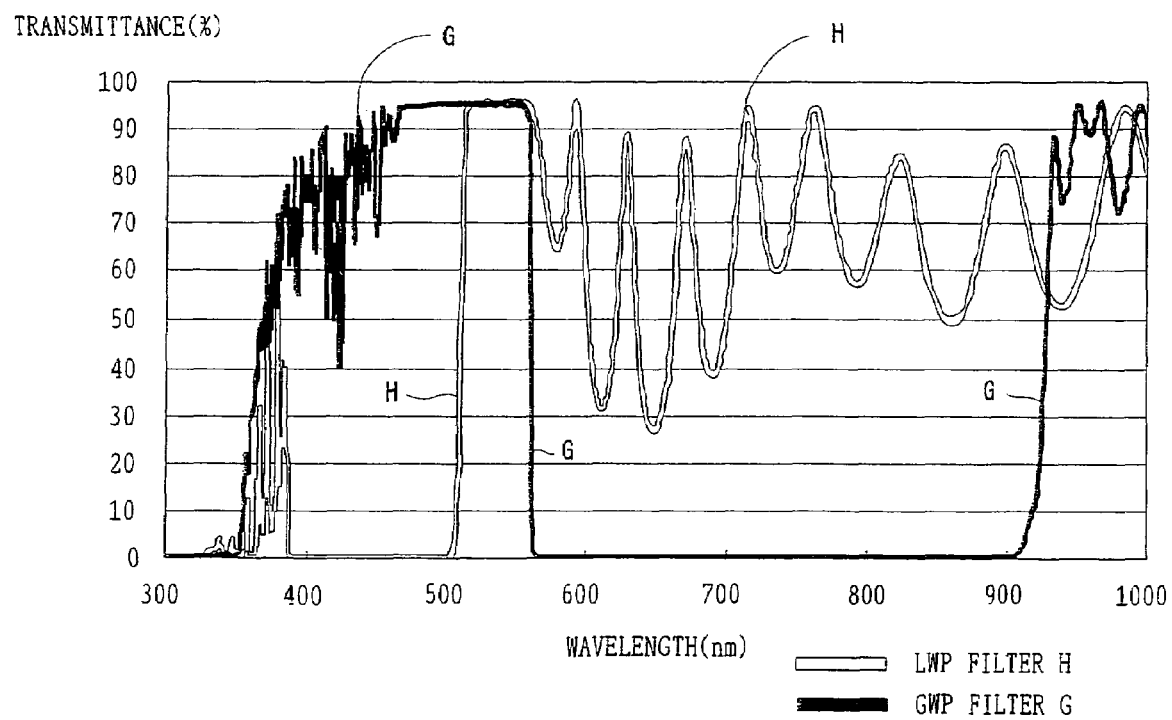
FIG. 14 is a graph showing optical characteristics of a long wave pass filter and a short wave pass filter which constitute the excitation filter 41 shown in FIG. 12.

As filters for cutting an unnecessary ultraviolet ray and infrared light composing the excitation filter 33, filters having the same film forming material and the film characteristic used in the first embodiment have been used, wherein filters I and K, each of which has two surfaces respectively are used by arranging the filter I at the position at which the filter J was arranged in the first embodiment, among filters I, J and K in the first embodiment. (Refer to FIG. 13) The characteristic of LWP filter H and SWP filter G are shown in FIG. 14.

SWP filter G having the largest influence to fluorescence observation performance has 90 layers composition in which film of $SiO_2$ (refractive index at wavelength of 400~650 nm is 1.46~1.47) and $Nb_2O_5$ (refractive index at wavelength of 400~650 nm is 2.26~2.48) are alternately laminated on the substrate, and it is formed by the RF sputtering method in which $SiO_2$ and $Nb_2O_5$ are used as start materials (target materials), respectively. Similarly, LWP filter H is formed by the RF sputtering method, and it has 54 layers composition in which film of $SiO_2$ (refractive index at wavelength of 400~650 nm is 1.46~1.47) and $Nb_2O_5$ (refractive index at wavelength of 400~650 nm is 2.26~2.48) are alternately laminated on the substrate.

The film compositions are shown in Table 7.

TABLE 7

| | Filter | Layer | λ | Film composition: from substrate side to air space side |
|---|---|---|---|---|
| Excitation Filter | I | 40 Layers | 365 nm | .4717H .8376L .9153H .8793L .877H 1.0091L .8576H .9991L .8887H 1.0232L .886H 1.014L .8922H 1.0237L .8876H 1.0155L .8893H 1.0257L .8982H 1.0224L .8956H 1.0322L .8956H 1.0027H .8765H 1.0474L .921H 1.0026L .8655H 1.0313L .9293H .9546L .9049H 1.0343L .9088H .8934L 1.0019H .7405L .9492H 1.7252L |
| | H | 32 Layers | 446 nm | .4636H .5368L .87H .7643L .6606H .8102L .7366H .8177L .7406H .8178L .738H .8172L .7425H .8222L .7451H .8248L .7465H .8236L .7434H .8205L .7412H .8216L .7443H .8218L .7403H .8174L .7392H .7664L .6448H .8143L .6443H 1.435L |
| | G | 126 Layers | 541 nm | .4129H 1.8825L .2515H 1.1383L 1.1756H .9966L .8251H 1.0511L 1.1333H 1.0346L .883H .8834L 1.0202H 1.0063L 1.0061H 1.0011L .994H .9758L .9597H .9585L .9896H .9882L .988H .9791L .9945H .9808L .9821H .9676L .9709H .9751L .9855H .9843L .9916H .9815L .9816H .9756L .9681H .9682L -982H .989L .9869H .981L .9787H .9763L .9775H .9725L .9756H .9788L .9875H .9843L .9813H .9765L .9752H .9736L .9764H .9781L .9859H .9873L .9827H .9746L .97H .9705L .9786H .983L .9853H .9825L .9827H .9768L .977H .9738L .978H .976L .9811H .977L .9838H .983L .9867H .9765L .9717H .9669L .9735H .9774L 1.0066H .9729L .9746H .9775L .9788H .9773L .9785H .9838L .985H .9781L .9698H .969L .99H .9903L .9927H .975L .927H .997L 1.0023H .9923L .9791H .9746L .9738H .9669L .9612H .9769L 1.04H .9833L .9917H .9386L .9565H .9997L 1.0011H .9861L .9959H 1.0112L .9943H .9635L .9787H 1.035L 1.056H 1.0458L .9806H .5042L |
| | J | 40 Layers | 630 nm | .104H .3641L 1.5729H .384L 1.5215H .6875L 1.282H .8823L 1.0826H 1.0057L 1.0206H .9786L 1.0308H .9762L 1.0251H .9748L 1.0268H .9744L 1.0243H .9731L 1.0248H .9728L 1.0228H .9715L 1.0238H .9738L 1.0243H .9731L 1.0266H .9794L 1.0311H .9817L 1.0349H .9883L 1.0627H .9913L 1.076H 1.0609L 1.0426H .5398L |
| | K | 46 Layers | 730 nm | .1138H .2459L 1.421H .1998L 1.3338H 1.0436L 1.0357H .9602L 1.0141H .9759L .978H 1.0107L .962H 1.0081L .9867H .9955L 1.0037H .9949L 1.0263H 1.0164L 1.039H 1.0074L 1.0086H 1.1092L 1.1082H 1.2087L 1.2397H 1.4037L 1.2535H 1.2343L 1.1688H 1.2798L 1.2738H 1.3348L 1.2873H 1.3122L 1.2015H 1.2358L 1.2137H 1.353L 1.353L 1.4123L 1.4016H 1.3646L 1.1353H .5852L |
| Absorption Filter | L | 148 Layers | 400 nm | .1635H 1.7085L .4484H .9814L .9552H .904L .785H 1.0077L 1.0924H 1.0178L .8801H .8507L .9695H .9719L .9872H . .9752L .9584H .9404L .9345H .9333L .942H .9475L .9574H .9524L .9653H .9465L .9496H .9435L .9505H .9519L .963H .9685L .9741H .9706L .9658H .9571L .9538H .9529L .9575H .9604L .9645H .9621L .9595H .9505L .9459H .9373L .9398H .9444L .9534H .9534L .9525H .9466L .947H .9478L .9543H .961L .9683H .9718L .9731H .9728L .9724H .9725L .9731H .9738L .975H .9754L .978H .989L .9838H .9826L .9835H .977L .9778H .9742L .9803H .9814L .9885H .9869L .9869H .9783L .9745H .9711L .9995H .9733L .9779H .9829L .9883H .9902L .9889H .9834L .9768H .9711L .9713H .9772L .9906H 1.0026L 1.0082H .9876L .9282H .9849L .9872H .9867L .9859H .9847L .9834H .9824L .9819H .982L 1.0101H .9445L .9845H .985L .985H .9843L .9832H .9818L .9807H .98L .9799H .9803L .981H .9816L .9816H .981L .9797H .9782L .9769H .9764L .977H .979L .9822H .9854L .9874H .987L .8849H .9338L .9751H 1.1998L 1.1464H .5093L 1.0826H .9426L 1.31H .7273L .8909H .7762L .9948H 1.6256L |
| | M | 80 Layers | 558 nm | .2775H 1.5503L 1.0703H 1.0726L .9993H 1.1179L 1.0027H 1.0121L 1.02H 1.0214L 1.0262H 1.0129L 1.0106H 1.0153L 1.0177H 1.0175L 1.0098H 1.0072L 1.0075H 1.0097L 1.012H 1.0131L 1.0102H 1.0091L 1.009H 1.0116L 1.0123H 1.0119L 1.009H 1.01L 1.0106H 1.0128L 1.0121H 1.0128L 1.0126H 1.0142L 1.0113H 1.0053L 1.0522H 1.0035L .9981H 1.04L 1.1189H .9539L 1.1072H 1.1909L 1.1473H 1.3243L 1.2349H 1.2112L 1.2337H 1.2739L 1.337H 1.2942L 1.2161H 1.251L 1.2768H 1.376L 1.268H 1.2399L 1.2147H 1.292L 1.3709H 1.304L 1.2415H 1.2255L 1.2774H 1.3699L 1.2765H 1.2549L 1.2012H 1.2868L 1.3763H 1.2818L 1.2507H 1.1177L 1.1156H 1.2743L .9869H .6999L |

Figure 15:
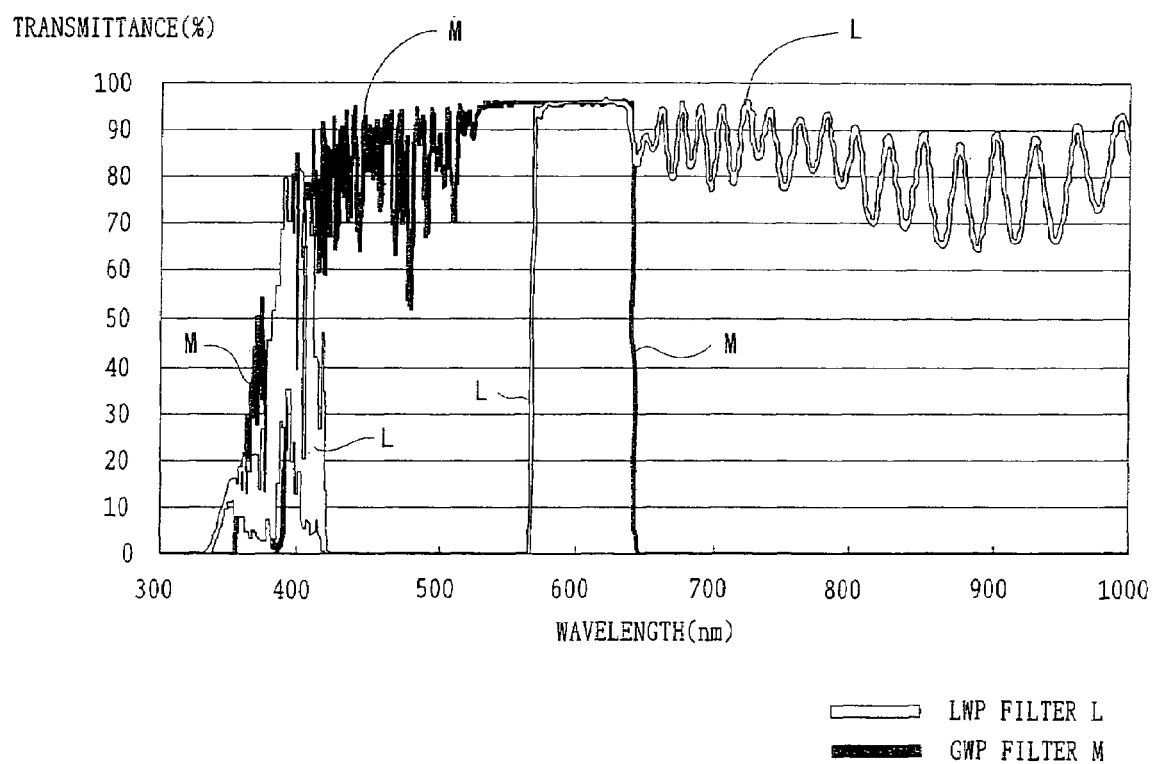
FIG. 15 is a graph showing optical characteristics of a long wave pass filter and a short wave pass filter which constitute the absorption filter 41 shown in FIG. 12.

In FIG. 7, $Nb_2O_5$ is set to H, and $SiO_2$ is set to L in the film composition of filters G and H. $Nb_2O_5$ is set to H and $SiO_2$ is set to L in the film composition of filters I, J and K. The absorption filter 41 is constructed by filters L and M on both sides of the substrate 441, in the same way as the first embodiment. Here, LWP filter L is composed of 130 layers by the RF sputtering method. Similarly, SWP filter M is formed of 90 layers by the RF sputtering method. Optical characteristics of wavelength range from 300 nm to 1000 nm about filters L and M are shown in FIG. 15.

As for optical characteristics of filters H, G, L, and M formed by the RF sputtering method, change of the half-value wavelength is 0~+0.5 nm when humidity changes from 10% to 95%, and in all cases, it is 0.5 nm or less.

Concretely, a test has been carried out by the following test conditions.

A substrate wherein each of filters H, G, L, and M formed by the RF sputtering method are formed only on one side on the substrate of BK7 respectively, and, the excitation filter 33 and the absorption filter 41 are prepared.

In a container in which silica gel is put, under an environment held at 10% of humidity and normal temperature (20° C.), after the substrate formed by films of filters H, G, L, and M as a film, the excitation filter 33 and the absorption filter 41 were exposed for four days, it was held in a constant temperature-humidity bath which is at 20° C. and 95% for 100 hours. Change of spectrum characteristic has been investigated before and after the test.

Change of the half-value wavelength before and after the test is shown in Table 8.

absorption filter 41 and at the long-wavelength side of the excitation filter 33 having the largest influence to fluorescence observation performance, when an interval between the half-value wavelength at the long wave side of the excitation filter 33 and the half-value wavelength at the short-wavelength side of an absorption filter 41 is set broad. In this embodiment, $Nb_2O_5$ is used. However, in case that $TiO_2$ and $Ta_2O_5$, or $Nb_2O_5$, or a mixture of one of these is used, the same effect was obtained by composing a filter film thickness by using the refractive index of these films.

In cases that the ion assist method, the ion plating method of the RF applying system or the ion beam sputtering method are used for forming filters H, G, L and M, instead of using the RF sputtering method, the same result has been obtained.

FIRST AND SECOND COMPARATIVE EXAMPLES

As comparative examples of the first embodiment and the third embodiment, the first and the second comparative examples are made by such a way that a film is formed only on one side on the substrate of BK7 by the vacuum evaporation method using $SiO_2$ (refractive index at the wavelength of 400~650 nm is 1.45~1.47), or $TiO_2$ (refractive index at the

TABLE 8

|  | Filter H | Filter G | Filter L | Filter M | Excitation Filter | | Absorption Filter | |
| --- | --- | --- | --- | --- | --- | --- | --- | --- |
|  |  |  |  |  | Short wavelength side | Long wavelength side | Short wavelength side | Long wavelength side |
| Before | 509.7 | 561.5 | 567.5 | 641.1 | 509.7 | 561.5 | 567.5 | 641.1 |
| After | 509.7 | 561.6 | 567.6 | 641.3 | 509.7 | 561.6 | 567.6 | 641.3 |
| Amount of change | 0.0 | 0.1 | 0.1 | 0.2 | 0.0 | 0.1 | 0.1 | 0.2 | unit: nm

According to the fourth embodiment even if a small number of layers is used, fluorescence is efficiently generated from a living tissue, and the observation can be efficiently achieved by using $Nb_2O_5$ having higher refractive index compared with $Ta_2O_5$ used in the first embodiment, as high refractive index materials at the short-wavelength side of the wavelength of 400~650 nm is 2.29~2.50) wherein the half-value wavelength is made to equal to the half-value wavelength of filter H in the first embodiment and the third embodiment.

The film compositions are shown in the following Table 9.

TABLE 9

| Filter | Layer | λ | Film composition: from substrate side to air space side |
| --- | --- | --- | --- |
| The first comparative example H | 54 layers | 457 nm | .7402H .2246L .5191H 1.5504H 1.1453H .5478L .6848H .6556L .7053H .7767L .857H .8891L .8515H .6819L .5828H .9274L .7852H .7995L .7907H .7973L .7752H .7906L .7781H .7897L .7744H .8002L .7763H .7891L .7741H .7983L .7914H .8038L .7841H .8006L .7934H .7843L .7566H .7731L .7722H .7973L .7881H .8127L .8117H .7858L .7947H .7813L .5139H .7856L 1.0456H .9833L .6587H .4989L .7024H 1.584L |
| The second comparative example H | 32 layers | 498 nm | .4636H .5368L .87H .7643L .6606H .8102L .7366H .8177L .7406H .8178L .738H .8172L .7425H .8222L .7451H .8248L .7465H .8236L .7434H .8205L .7412H .8216L .7443H .8218L .7403H .8174L .7392H .7664L .6448H .8143L .6443H 1.435L |

Figure 16:
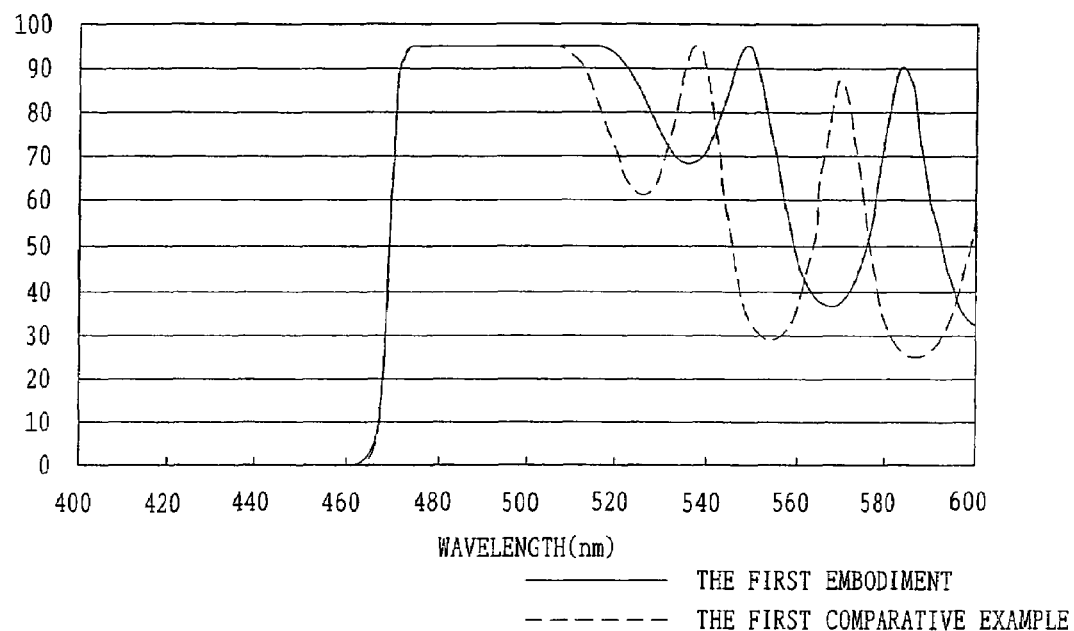
FIG. 16 is graph showing in comparison with spectrum characteristics of long wave pass filter which constitute excitation filters in the first embodiment and the first comparative example.
Figure 17:
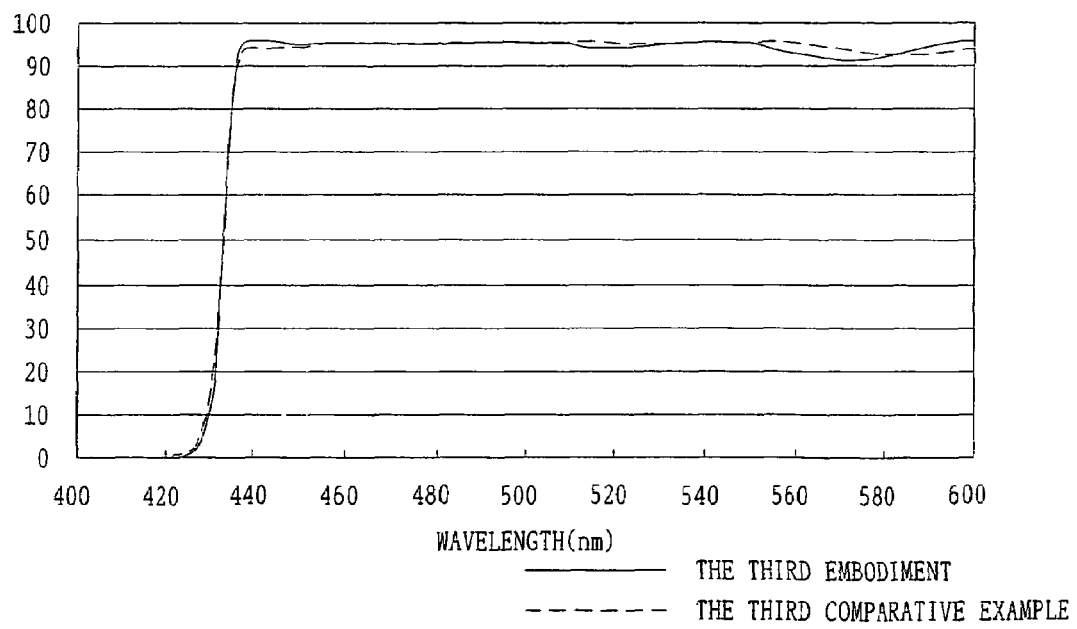
FIG. 17 is graph showing in comparison with spectrum characteristics of long wave pass filters which constitute excitation filters in the third embodiment and the second comparative example.
Figure 18:
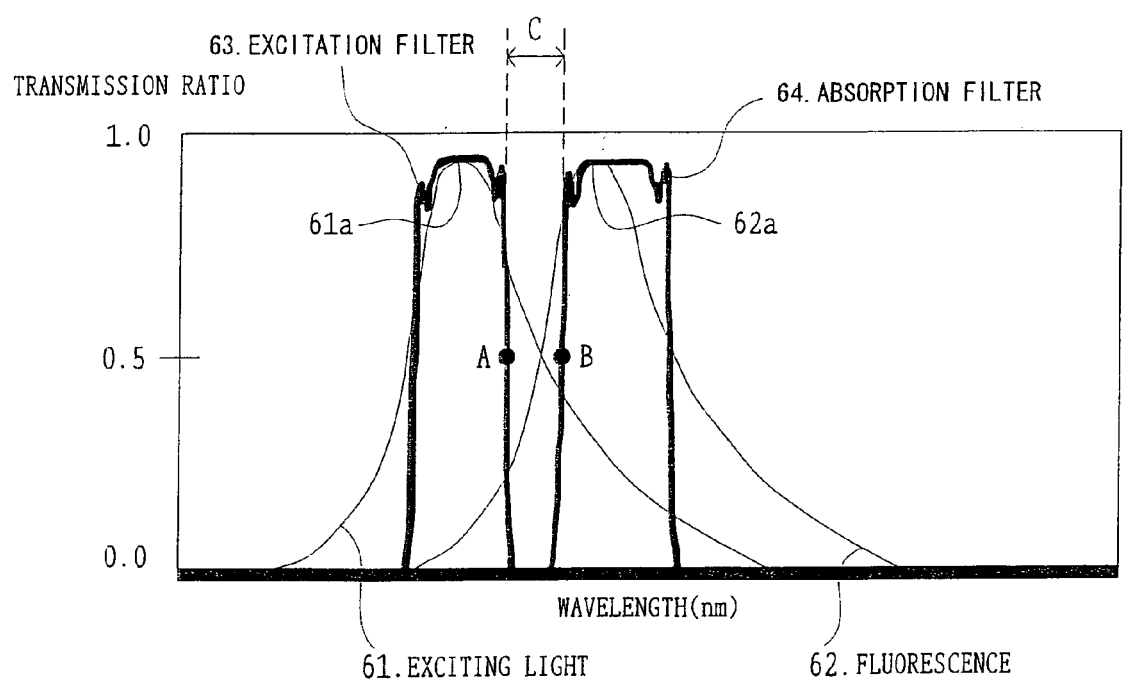
FIG. 18 is a graph of spectrum characteristics showing exemplarily relations in which fluorescence in a wavelength range of longer wavelength than a wavelength range of the exciting light is generated by irradiation of the exciting light to a specimen, when a fluorescence observation is carried out by irradiating the exciting light having a predetermined spectrum characteristic.

With respect to LWP filter H which composes the excitation filter 33, a spectrum characteristic in the first comparative example in comparison with the first embodiment is shown in FIG. 16 and a spectrum characteristic in the second comparative example in comparison with the third embodiment is shown in FIG. 17.

With respect to these substrates, the amount of change of the half-value wavelength when changing humidity from 10% to 95% is shown in the following Table 10.

TABLE 10

|  | The first comparative state Fiter H | The second comparative state Filter H |
|---|---|---|
| Before | 509.7 | 561.5 |
| After | 509.7 | 561.6 |
| Amount of change | 0.0 | 0.1 | unit: nm

In the first and the second comparative examples, since change owing to humidity is large compared with the characteristics of the first and the third embodiments, an interval between the half-value wavelength at the long wave side of the excitation filter and the half-value wavelength at the short-wavelength side of an absorption filter must be kept broad when applying the excitation filter and the absorption filter for fluorescence observation.

Fifth Embodiment

In the fifth embodiment, the absorption filter in the third embodiment is used instead of using the absorption filter 54 in the second embodiment. Moreover, the specimen 53 was changed into a specimen in which fluorescence is generated by the laser light 51 having the wavelength of 451.1 nm and an intensity of 800 mW from the laser source.

The wavelength of the laser light 51 is 451.1 nm and the half-value wavelength at the short-wavelength side of the absorption filter 54 is 462.8 nm, and a wavelength width which is an interval between the half-value wavelength at the wavelength of the laser light 51 and the short-wavelength side of the absorption filter 54 is 11.7 nm. Therefore, the fluorescence generated from the specimen 53 was able to be picked up efficiently, and measurement was able to be made by the light receiving portion 55 in high sensitivity state.

Sixth Embodiment

In the sixth embodiment, the absorption filter in the fourth embodiment is used instead of using the absorption filter 54 in the second embodiment. Moreover, the specimen 53 was changed into a specimen 53 in which fluorescence is generated by the laser light 51 having the wavelength of 563.5 nm and an intensity of 800 mW from the laser source.

The wavelength of the laser light 51 is 563.5 nm and the half-value wavelength at a short-wavelength side of the absorption filter 54 is 567.5 nm, and a wavelength width which is an interval between the half-value wavelength at the wavelength of the laser light 51 and the short-wavelength side of the absorption filter 54 is 4 nm. Therefore, the fluorescence generated from the specimen 53 was able to be picked up efficiently, and measurement was able to be made by the light receiving portion 55 in high sensitivity state.

The invention claimed is:

1. An apparatus for fluorescence observation comprising laser light used as exciting light, and an absorption filter which blocks the exciting light and transmits only fluorescence generated from a specimen irradiated with the exciting light,
wherein the absorption filter includes a multilayer film having 90 or more film layers, and an interval between a wavelength of the laser light and a half-value wavelength of the absorption filter on a short-wavelength side is within a width between 1 nm to 12 nm.

2. The apparatus for fluorescence observation according to claim 1, wherein the interval between the wavelength of the laser light and the half-value wavelength of the absorption filter on the short-wavelength side is within a width between 6 nm to 12 nm.

3. The apparatus for fluorescence observation according to claim 1, wherein change of the half-value wavelength of the absorption filter when humidity changes from 10% to 95%, is 0.5 nm or less.

4. The apparatus for fluorescence observation according to claim 1, wherein the multilayer film of the absorption filter is laminated of alternately arranged low refractive index films made of $SiO_2$ and a high refractive index films made of one of or any mixture of $Ta_2O_5$, $Nb_2O_5$ and $TiO_2$, and the multilayer film is applied to at least one surface of a substrate of the absorption filter.

* * * * *

UNITED STATES PATENT AND TRADEMARK OFFICE
CERTIFICATE OF CORRECTION

| | | |
|---|---|---|
| PATENT NO. | : 7,453,568 B2 | Page 1 of 1 |
| APPLICATION NO. | : 10/533687 | |
| DATED | : November 18, 2008 | |
| INVENTOR(S) | : Kawamata et al. | |

It is certified that error appears in the above-identified patent and that said Letters Patent is hereby corrected as shown below:

Column 26, line 41, change "a high refractive index films" to -- high refractive index films --.

Signed and Sealed this

Twenty-fourth Day of March, 2009

JOHN DOLL
*Acting Director of the United States Patent and Trademark Office*